US012806413B2

(12) United States Patent
Wolf et al.

(10) Patent No.: US 12,806,413 B2
(45) Date of Patent: Nov. 24, 2026

(54) ADVANCED IMPLANTABLE ENDOVASCULAR, LOW PROFILE INTRACARDIAC LEFT ATRIAL RESTRAINING DEVICES FOR LOW ENERGY ATRIAL CARDIOVERSION, PACING AND SENSING

(71) Applicant: Wolf Cardio, LLC, Houston, TX (US)

(72) Inventors: Randall K. Wolf, Houston, TX (US); Paul Spence, Aventura, FL (US)

(73) Assignee: Wolf Cardio, LLC, Houston, TX (US)

( * ) Notice: Subject to any disclaimer, the term of this patent is extended or adjusted under 35 U.S.C. 154(b) by 445 days.

(21) Appl. No.: 18/173,015

(22) Filed: Feb. 22, 2023

(65) Prior Publication Data

US 2023/0264017 A1 Aug. 24, 2023

Related U.S. Application Data

(60) Provisional application No. 63/312,773, filed on Feb. 22, 2022.

(51) Int. Cl.
*A61N 1/05* (2006.01)
*A61B 17/00* (2006.01)

(52) U.S. Cl.
CPC .......... *A61N 1/057* (2013.01); *A61B 17/0057* (2013.01); *A61B 2017/00606* (2013.01); *A61B 2017/00867* (2013.01)

(58) Field of Classification Search
None
See application file for complete search history.

(56) References Cited

U.S. PATENT DOCUMENTS 5,755,761 A 5/1998 Obino
5,855,592 A * 1/1999 McGee ................ A61N 1/3918 600/374
6,516,231 B1 2/2003 Flammang
(Continued)

FOREIGN PATENT DOCUMENTS

CN 106362288 A 2/2017
WO WO-95/10226 A1 4/1995
(Continued)

OTHER PUBLICATIONS

International Search Report on PCT/US2020/63664 dtd Mar. 10, 2021, 3 pgs.
(Continued)

*Primary Examiner* — Michael W Kahelin
(74) *Attorney, Agent, or Firm* — Foley & Lardner LLP

(57) ABSTRACT

Disclosed are various configurations of electrodes with accompanying extensions and wires configured to be attached at or near the left atrium of a heart to allow the device to be held snug against the endocardium and out of the blood flow for low energy defibrillation of the atria in response to atrial fibrillation or other atrial arrhythmias. The portion of the lead internal to the atrium (e.g., the left atrium) is restrained against the endocardium of the left atrium by way of a restraint mechanism. In one example, the electrode is configured to attach to the atrial septum, with wires containing memory-shaped metal to keep the wires against the heart wall. In yet another example, the electrode is configured to be part of a mitral valve device.

20 Claims, 34 Drawing Sheets

(56) References Cited

U.S. PATENT DOCUMENTS

| | | | | |
|---|---|---|---|---|
| 7,448,999 | B1 | 11/2008 | Karicherla et al. | |
| 7,515,971 | B1 * | 4/2009 | Doan | A61B 5/0215 600/375 |
| 8,021,359 | B2 | 9/2011 | Auth et al. | |
| 8,543,193 | B2 | 9/2013 | Satin et al. | |
| 8,849,384 | B2 | 9/2014 | Greenspan | |
| 9,492,657 | B2 | 11/2016 | Gerber | |
| 2005/0119647 | A1 | 6/2005 | He et al. | |
| 2006/0041300 | A1 | 2/2006 | Zhang et al. | |
| 2007/0073179 | A1 | 3/2007 | Afonso et al. | |
| 2009/0198297 | A1 | 8/2009 | Zhang et al. | |
| 2010/0317981 | A1 | 12/2010 | Grunwald | |
| 2012/0172944 | A1 | 7/2012 | Dori et al. | |
| 2013/0331920 | A1 * | 12/2013 | Osypka | A61N 1/0587 607/122 |
| 2014/0207202 | A1 | 7/2014 | Imran | |
| 2016/0325079 | A1 | 11/2016 | Osypka | |
| 2016/0354600 | A1 | 12/2016 | Kolberg et al. | |
| 2017/0281031 | A1 | 10/2017 | Houben et al. | |
| 2018/0296842 | A1 | 10/2018 | Imran | |
| 2020/0054882 | A1 | 2/2020 | Dale et al. | |
| 2020/0138319 | A1 | 5/2020 | Spector | |
| 2021/0369394 | A1 | 12/2021 | Braido et al. | |
| 2023/0264017 | A1 | 8/2023 | Wolf et al. | |

FOREIGN PATENT DOCUMENTS

| | | | | |
|---|---|---|---|---|
| WO | WO-2018/085545 | A1 | 5/2018 | |
| WO | WO 2021/113843 | * | 6/2021 | A61N 1/05 |
| WO | WO-2021/113843 | A1 | 6/2021 | |
| WO | WO-2022/076801 | A1 | 4/2022 | |

OTHER PUBLICATIONS

International Search Report and Written Opinion on PCT/US2023/063074 dated Oct. 10, 2023, 13 pgs.

* cited by examiner

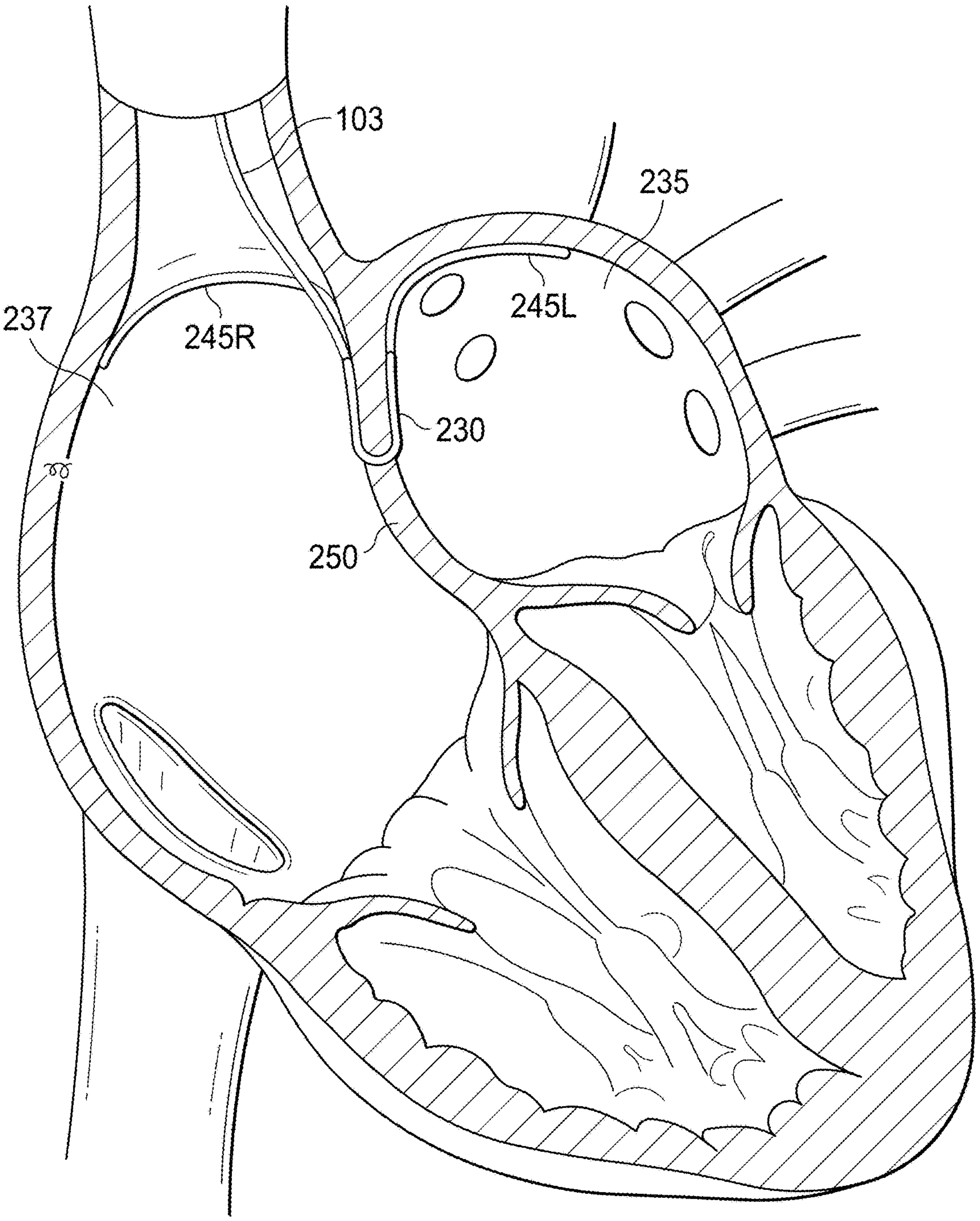
FIG. 2I
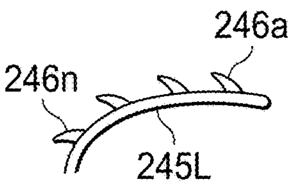
FIG. 2I-A
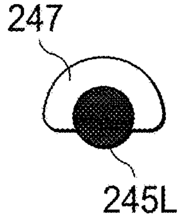
FIG. 2I-B

ADVANCED IMPLANTABLE ENDOVASCULAR, LOW PROFILE INTRACARDIAC LEFT ATRIAL RESTRAINING DEVICES FOR LOW ENERGY ATRIAL CARDIOVERSION, PACING AND SENSING

RELATED APPLICATIONS

This application claims priority to co-pending U.S. Provisional Patent Application having Ser. No. 63/312,773 filed on Feb. 22, 2022; the contents of which are hereby incorporated by reference in their entirety.

BACKGROUND OF THE INVENTION

Wires placed in the heart connected to pacemakers have been used in the right side of the human heart since 1957 (Earl Bakken-founder of Medtronic). Since then millions of wires for sensing, pacing and defibrillating the heart have extended and saved lives around the world. Despite this body of work, wires are not used on the left side of the heart. Mitral valve devices, left atrial occlusion devices, and septal occlusion devices have been placed on the left side of the heart for decades.

However, wires traditionally have not been placed on the left side of the heart because of the risk that a thrombus collecting on a wire floating free in the heart can detach. If the wire is on the right side of the heart, and a thrombus develops and detaches, the thrombus can only travel to the lungs, and intrinsic enzymes can be used to break down the thrombus or clot. However, if a wire is on the left side of the heart and a thrombus develops and detaches, the clot will travel into the aorta and to the brain. The brain has no intrinsic mechanism to dissolve the clot, and a stroke can occur, which can be devastating.

Defibrillating the human heart has saved many lives. Initially performed only externally (through the skin), defibrillators are now placed internally (endovascular and intracardiac and extracardiac) to emergently defibrillate the heart to terminate dangerous arrhythmias. Current defibrillators need relatively high energy (as measured in joules) to defibrillate the heart. These shocks are painful to the patient and cause incredible anxiety. The energy utilized wears down the batteries quickly, which then require replacing. Replacing the generators and batteries are expensive (the batteries are incorporated into the generators) and there is the risk of infection with generator and battery replacement. Infections are sometimes fatal and are very expensive to the medical system.

Atrial fibrillation (AF), the most common human cardiac arrhythmia, causes great morbidity, mortality and cost. Although AF is present only in the atrial chambers of the heart today the entire heart is defibrillated for AF because leads to the heart for defibrillation generally do not include leads placed in the left atrium (LA). Accordingly, it is difficult to sense the LA for the occurrence of arrhythmias and difficult to selectively defibrillate the LA. As such, defibrillating the heart in response to AF generally requires defibrillating the entire heart.

SUMMARY OF THE INVENTION

The embodiments described herein pertain to various configurations of low profile electrodes and accompanying structures that hold the electrodes and wires against the endocardium (eliminating free floating wires) and configured to be attached at or near the left atrium of the heart to allow for low energy recording, sensing, pacing, and/or defibrillation of both atria in response to atrial fibrillation or other atrial arrhythmias. The electrodes are attached to the septum of the atria in a position that is favorable for easy and secure deployment, maintaining a low profile placement. This attachment also allows for repeated crossing of the intra atrial septum at later dates, for additional ablation procedures or placement of additional closure or valve devices. The novel device can be fitted with a radio-opaque marker to facilitate later crossing of the intra atrial septum.

In addition to defibrillating the upper chambers of the heart, these electrodes and accompanying structures can be utilized to sense and map normal and abnormal electrical impulses. The devices can also be used in conjunction with leads implanted in the right atrium, the right ventricle, the coronary sinus, leads attached to other devices in the atria, and leads on the outside of the heart. In one embodiment, the electrode is configured to attach to the atrial septum, with the wire attachment that holds the wires against the heart tissue. In another embodiment, the electrode configuration is attached to a modified atrial septal closure device, could also be an atrial septal opening device, again with the special attachment keeping the wires held fast against the heart wall. In another embodiment, the electrode is configured to be part of an atrial appendage closure device, also with the special attachment that keeps the wire from free floating, on either the inside (endocardial surface) or outside (epicardial surface) of the heart. In yet another embodiment the electrode is configured to be part of a mitral valve device, or may be incorporated into any valve repair or replacement device, whether placed by conventional open heart surgery or by an endovascular technique.

A beneficial feature is that these embodiments allow the electrodes and wires to be held fast against the heart tissue, which like mitral devices commercially available, avoid thrombus formation on the electrodes and wires. The described devices then allow sensing, pacing and/or defibrillation of the left side of the heart that has not been clinically addressed before. For instance, these devices could be used to directly pace the left atrium. Traditionally, only the right atrium can be accessed for pacing. In many patients, because of intrinsic conduction issues or distension of the atria, the right atrial pacing is not always in synch with the left atrium. With the new device in the intra atrial septum, the left atrium or about the left atrium—in clinical practice both atria can be paced. This could allow for synchronous bi-atrial pacing, which improves the efficacy of atrial pacing and would improve cardiac output and ejection fraction in some patients.

BRIEF DESCRIPTION OF THE FIGURES

For a detailed description of various examples, reference will now be made to the accompanying drawings in which:

FIGS. 2I-2M are illustrations of illustrative alternative embodiments of electrical electrodes and sub-processes for implantation thereof that may be used in conjunction with a septal electrode.

DETAILED DESCRIPTION OF THE INVENTION

Figure 1:
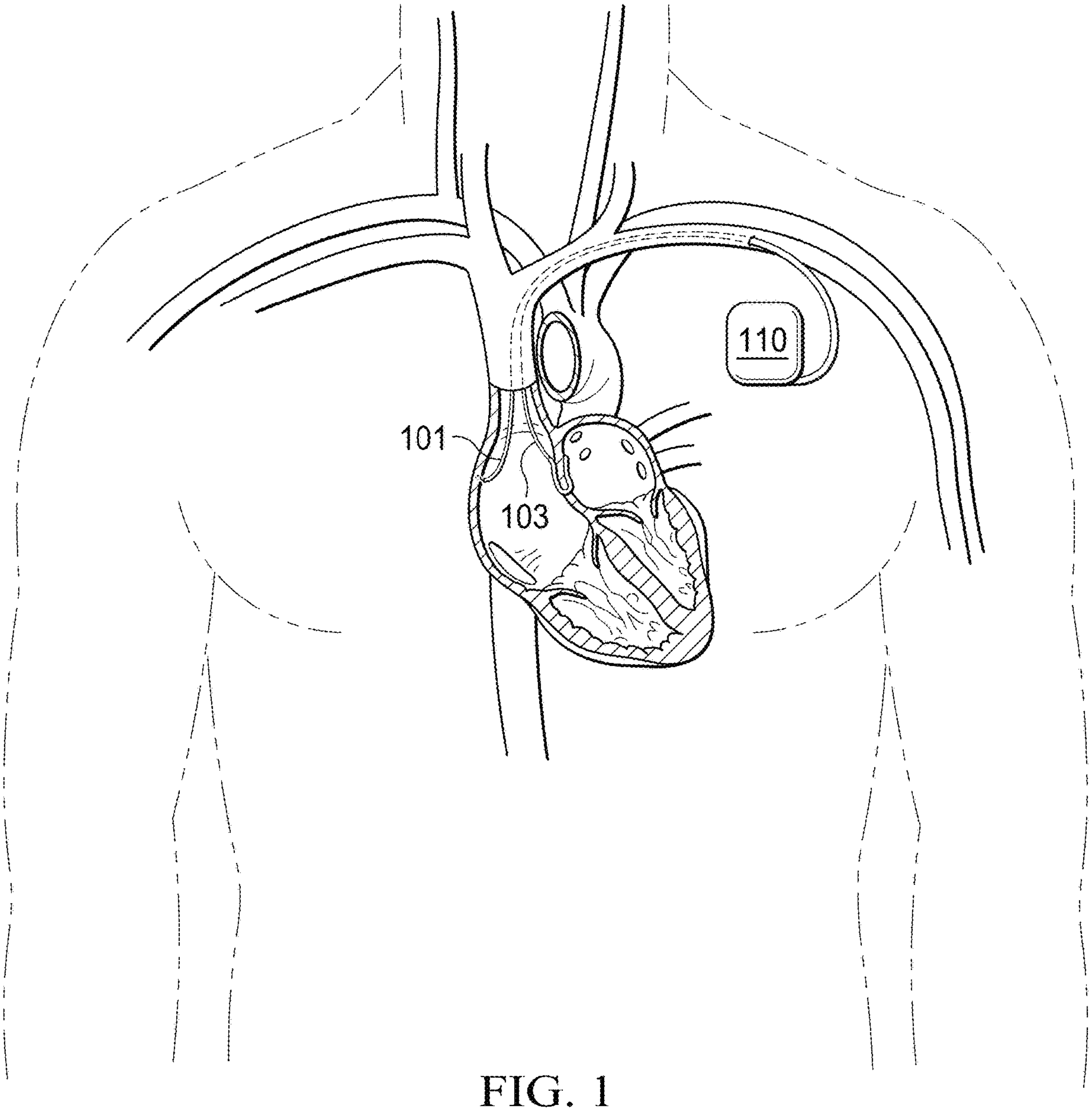
FIG. 1 illustrates a septal electrode attached to the atrial septum, and its extensions which keep the wires against the heart tissue.

Low profile restraining devices are described herein which eliminate the problem of current intracardiac leads which generally are permitted to free float within the interior volume of the corresponding cardiac chamber. The described embodiments include a mechanism that keep a portion of the lead fixed against the endocardium of the left atrium, where the electrode and lead will become embedded against the wall of the heart. Thus, thrombus is avoided with the described low-profile devices on the left side of the heart. Placement of the leads, with these devices, on the left side of the heart facilitates new therapies for the treatment of cardiac disease. The restraint mechanisms described herein can be extended to other chambers of the heart. The device allows for repeat crossing of the septum. Indeed, with a radio-opaque marker on the septal portion of the device, repeated crossing of the septum may be made more quickly and safely.

Beneficially, the described examples are directed to leads connected to the left atrium. For atrial arrhythmias (arrhythmias in the upper chambers of the heart), left atrial leads are a better way to sense AF and selectively defibrillate the upper chambers. A much lower energy can be used (1-10 joules) compared to defibrillating the entire heart. Accordingly, the patient experiences much less discomfort and battery life is increased. Leads in the LA can also provide a record of where the AF is initiating, which could guide further treatment to eliminate the focus. A left atrial lead requires careful design to avoid thrombus and embolism. The embodiments described herein pertain to a device placed entirely by a percutaneous route. The device is low profile and sits flat against the endocardial wall and becomes strongly embedded in tissue. The low-profile nature of the device avoids or reduces the risk of thrombus formation. The described device provides a solution for sensing and treating AF and other supraventricular arrhythmias, with lower power, and with shocks that are less painful or pain-free to the patient.

The embodiments described herein pertain to an implantable device that is connected to wires that contain nitinol or other types of shape memory metal or plastic or other metal or metal alloy or combination that creates some grasp against the septum and torsion that keeps the wires against the walls of the heart and prevents free floating wires. These devices can be placed in or around the left atrium of the heart, as well as on the right side of the heart. The restraining device applies passive force to the tissue by a curved wire bent to a looped state to provide a suitable amount of torsion. The devices can have protrusions to hold the device in place and prevent slippage until tissue healing occurs. The electrode portion of the device can be coated with materials such as gold to increase its conductivity. Incorporated into the curved wire is an extension of conducting wire, also coated with a material to improve conduction (such as gold plating), to increase the surface area of the device. Beneficially, the extension will lie against the heart tissue, because of wire torsion. The device is also incorporated with insulated wire(s) that will hug the heart wall. The insulated portion of the device will have an outer nitinol or other shape metal or plastic or other metal or composite that keeps the wires out of the blood stream. As in other devices in the heart that abut the endocardial surface, this device and its extensions and will become incorporated into the atrial tissue and will remain out of the flow of blood through the heart.

The devices then exit the heart, as with commercially available devices, to connect to a pacemaker, defibrillator or transducer or some combination of the these. This allows the device to receive and transmit an electrical charge from a remote site, such as a transducer or pacemaker. The transducer and pacemaker devices are available from several manufacturers, such as Medtronic and St. Jude Medical. The device sits flat against the atrial septal wall and becomes strongly embedded in tissue. This low profile discourages thrombus formation, and therefore allows the devices to be placed on the left side of the heart. In clinical practice, the devices with the extensions can be used on the right side of the heart also. The device has excellent electrical contact. The restraining device is held passively against the atrial septum. The unique property of the restraining device easily attaching to the atrial septum with a low profile provides a safe route for deployment. Since the extensions and the wires are constructed with a shaped memory metal or other material that holds the extensions and wires against the endocardium, the device can be deployed on the left side of the heart.

Currently transseptal punctures are commonplace during electrophysiologic (EP) studies. The wires for deployment of the device, such as a transseptal sheath and guidewire and obturator are already ideally situated during the transseptal puncture, which is utilized to enter the left atrium. Usually these EP studies are for the treatment of AF, including mapping and ablation and closure of the left atrial appendage, so it is straight-forward to place the restraining device during an EP procedure. Prior ways to achieve good electrical contact inside the heart include screws, barbs, hooks, pins and electrode plates. All these can be incorporated into the distal restraining device and to the extensions and special wires to help hold the devices against the heart wall. This also ensures good electrical contact. The device can incorporate coatings such as steroids to prevent fibrosis, low contact or high energy. The device can include a bioabsorbable component, such that after the electrode becomes embedded in tissue, the remaining restraining portion of the device reabsorbs. The device may also contain an antithrombotic coating, which helps prevent thrombus formation until the device is surrounded by tissue ingrowth. The device is carefully designed to be low profile, but with enough strength in the deployed position to provide complete stability in the intra-atrial septum. The restraining device on the septum may also contain material to cause certain portions of the device to be radio-opaque so as to guide later access to transeptal punctures, which may render future transeptal punctures faster, easier, and safer.

The restraining device can be integrated into any other device placed in or around the left or right atrium. The restraining device can be modified to work with any device that is to be placed in or around the right or left atrium, including, but not limited to atrial septal closure devices, left atrial closure devices (both intra and extracardiac) and valve repair or replacement devices. In the case of a septal occlusion device, the restraining device is modified to be incorporated into the rings of the septal closure device. Several possible iterations include three electrode conducting rings around the areas of the septal device that abut the endocardium of the septum. The exact configuration of the wire array can be changed depending on the device configuration, the surface area in contact, and the resistance generated. In the case of a mitral valve replacement, the retraining device can be modified to fit in a groove where the valve device abuts atrial tissue. The wire electrodes of the device may be circular or may be cross-hatched, or other configuration to provide the therapeutically sufficient electrical output at the lowest energy with a suitable resistance profile.

The retraining device could be delivered together with the valve or separately. The distal end of the lead can be affixed to, for example, the atrial septum, in or around the left atrial appendage, or in a mitral valve device. This allows for low energy defibrillation of the atria in response to atrial fibrillation or other atrial arrhythmias. The device can also be used to sense electrical activity on the endocardial surface. This information may be recorded and stored for determining the earliest site and other sites of atrial arrhythmias. This information may then direct treatment either with the device, for termination of the arrhythmia by pacing or other electrical stimulation through the device, and/or for later treatment with ablation during an EP procedure.

It can be used in conjunction with other leads and wires in both atria of the heart, or left atria and either right ventricle, left ventricle or coronary sinus that can be used to defibrillate the atria. It can be used in conjunction with electrodes on the outside of the heart as well, such as epicardial leads and electrodes. A lead placed inside the atria can facilitate defibrillation using a relatively low energy (1-10 Joules, J) waveform, delivered in many different ways, to reliably defibrillate or pace the atria.

The lead and accompanying extensions and wires can be placed into the patient via blood vessels in the groin, neck, or other areas. The distal region of the lead has electrodes and is placed in or around the left atrium (e.g., atrial septum, in or around the left atrial appendage, or in a mitral valve device). The wire configuration keeps the wires against the heart walls. The proximal end of the wire can be connected to a small defibrillator unit or a transducer that is placed subcutaneously in the patient. Such pacemakers and defibrillators can sense, pace and defibrillate. Because of the novel placement of the device, the upper chambers of the heart, the atria, can be selectively defibrillated, allowing for a very low energy defibrillation. The device also allows for sensing directly in the left atrium, which could be used to detect the origin of arrhythmias and could be used to selectively pace the left atrium in many configurations. If a transducer is used, power can be transferred to the transducer transcutaneously from an external device.

In one embodiment and as noted above, a restraining device is used to hold the left atrial wire in place against the atrial septum. A restraining device is a passive mechanical device that allows atrial defibrillation of both atria. Two devices are illustrated in FIGS. 1-4B. One is a device that has a spring effect to provide adequate restraining force to hold the wire in place against the septum, but without damaging the septum. This device can have protrusions to help hold the device in place and prevent slippage until healing occurs. This device can have extensions to provide for additional surface area for optimal sensing, pacing, and defibrillation. The extensions contain memory shaped metal or other similar substance to provide torsion, which keeps the extensions against the walls of the heart and out of the flow of blood through the heart. The second device is an array that attaches to or replaces an atrial septal defect closure device. Both can be placed in the patient at the end of a medical procedure such as a catheter ablation procedure to treat atrial fibrillation, or as a stand-alone procedure. Through a combined groin and subclavian approach (the left subclavian approach is illustrated), the wires placed from the groin can be brought to the subcutaneous position in the subclavian area, and then the defibrillator device can be placed.

FIG. 1 depicts an arrangement of the leads with one cardiac atrial lead 101 placed in the right atrium (similar to the atrial lead of a dual chamber pacing configuration). Part of this embodiment is the placement of a second cardiac atrial lead 103 (the device) in the left atrium, which allows for specific atrial sensing, pacing, and/or defibrillation, with a very small amount of energy (approximately 1-10 joules). The distal end of the left atrial lead 103 includes a shape memory structure or other solid or composite material that is configured to hold a portion of the lead 103 against a person's endocardium. The shape memory structure in this example is configured to be restrained to opposites sides of the atrial septum.

FIG. 1 also shows an electronics enclosure 110 which comprises a sealed enclosure containing a battery and a circuit. In one example, the circuit can generate the stimulation energy to electrodes at the distal region of the lead(s) 101, 103 for pacing and/or for defibrillation. The circuit additionally or alternatively can sense and record the electrical activity from the electrode(s). The electronics enclosure device 110 may be a pacemaker, a defibrillator, a device that both paces and defibrillates, and/or a sensing or recording device.

Figure 2A:
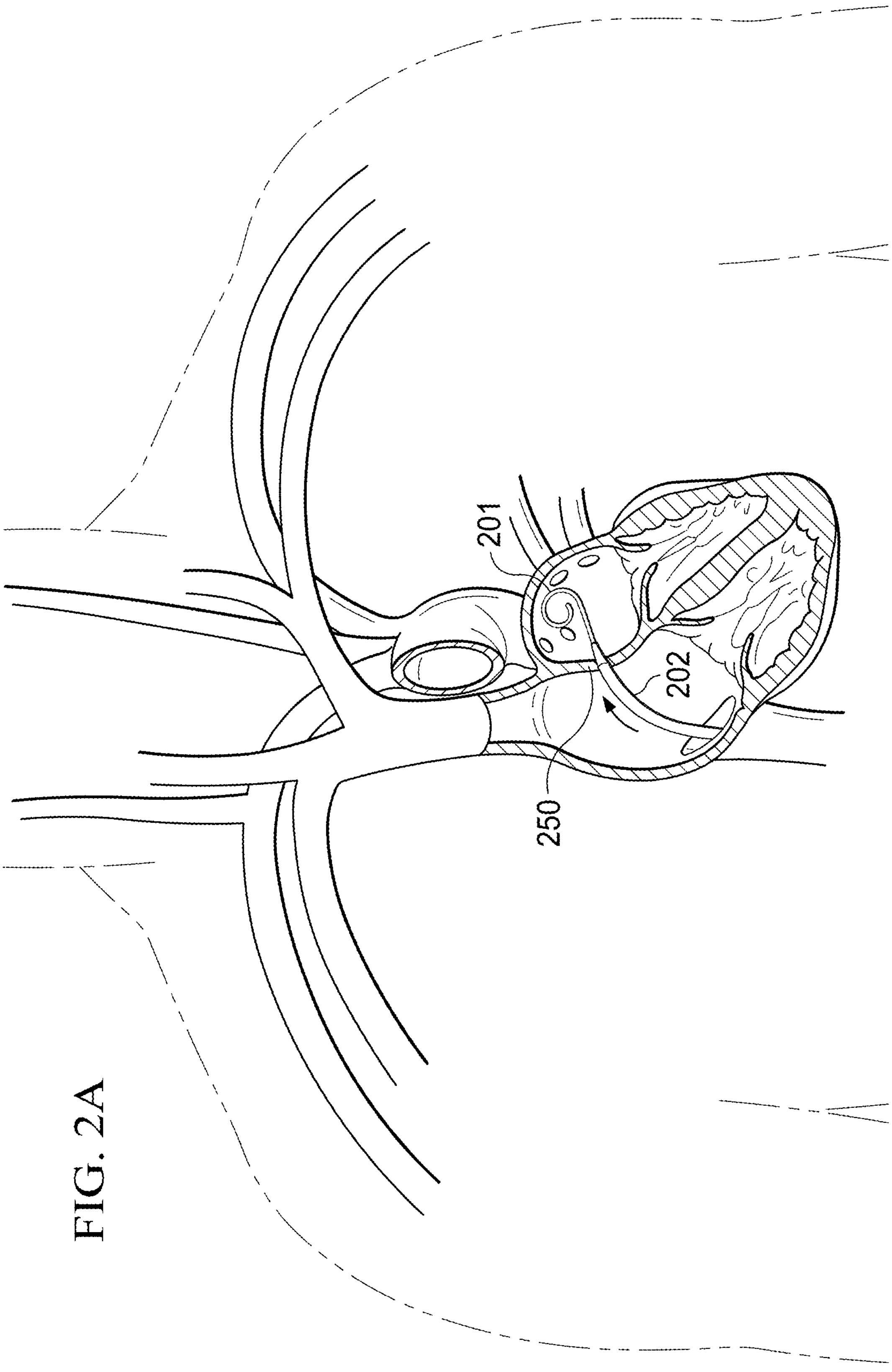
FIGS. 2A-2H illustrate a sequence of steps to attach the septal electrode during a surgical procedure.
Figure 2B:
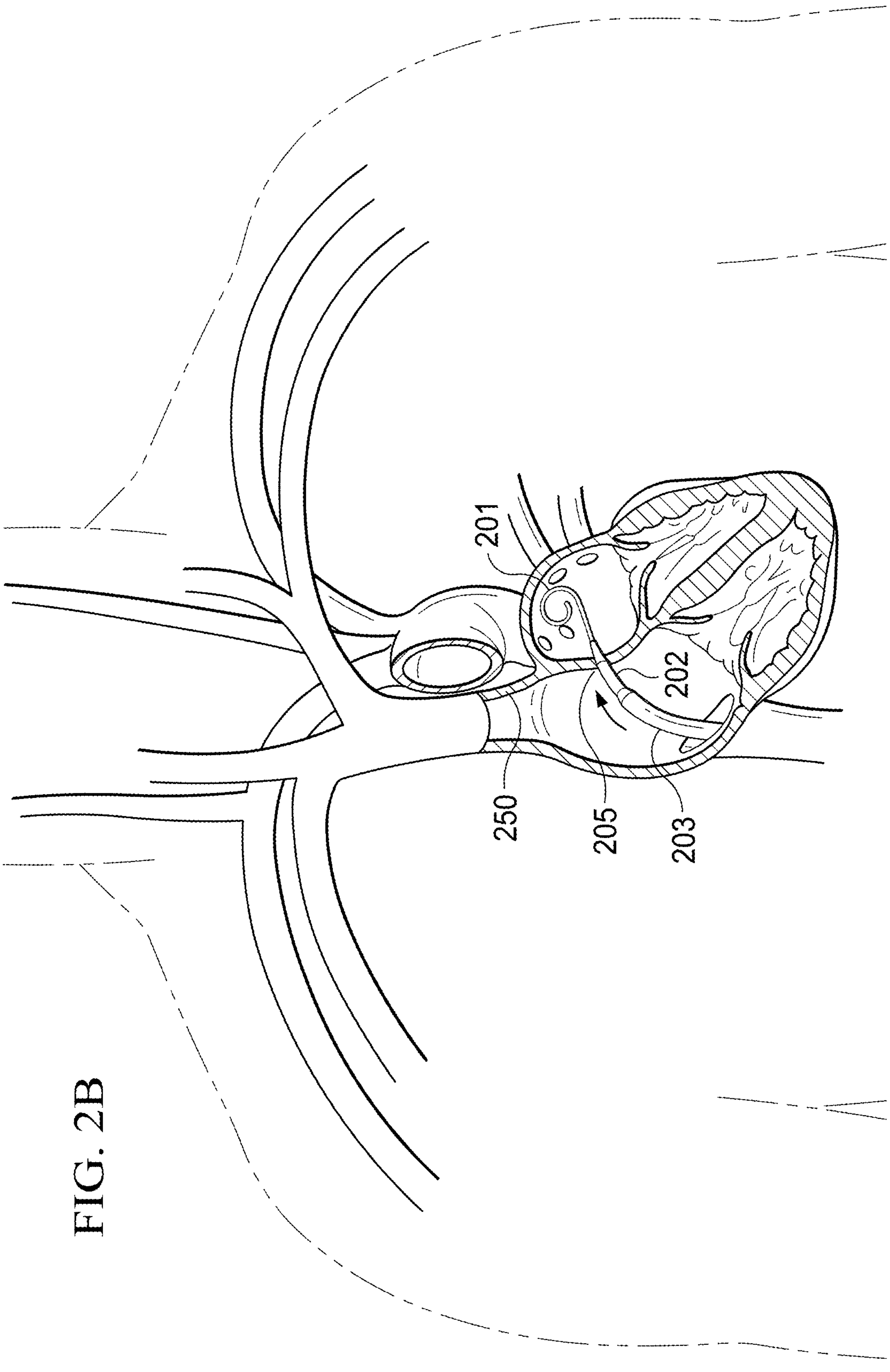
Figure 2C:
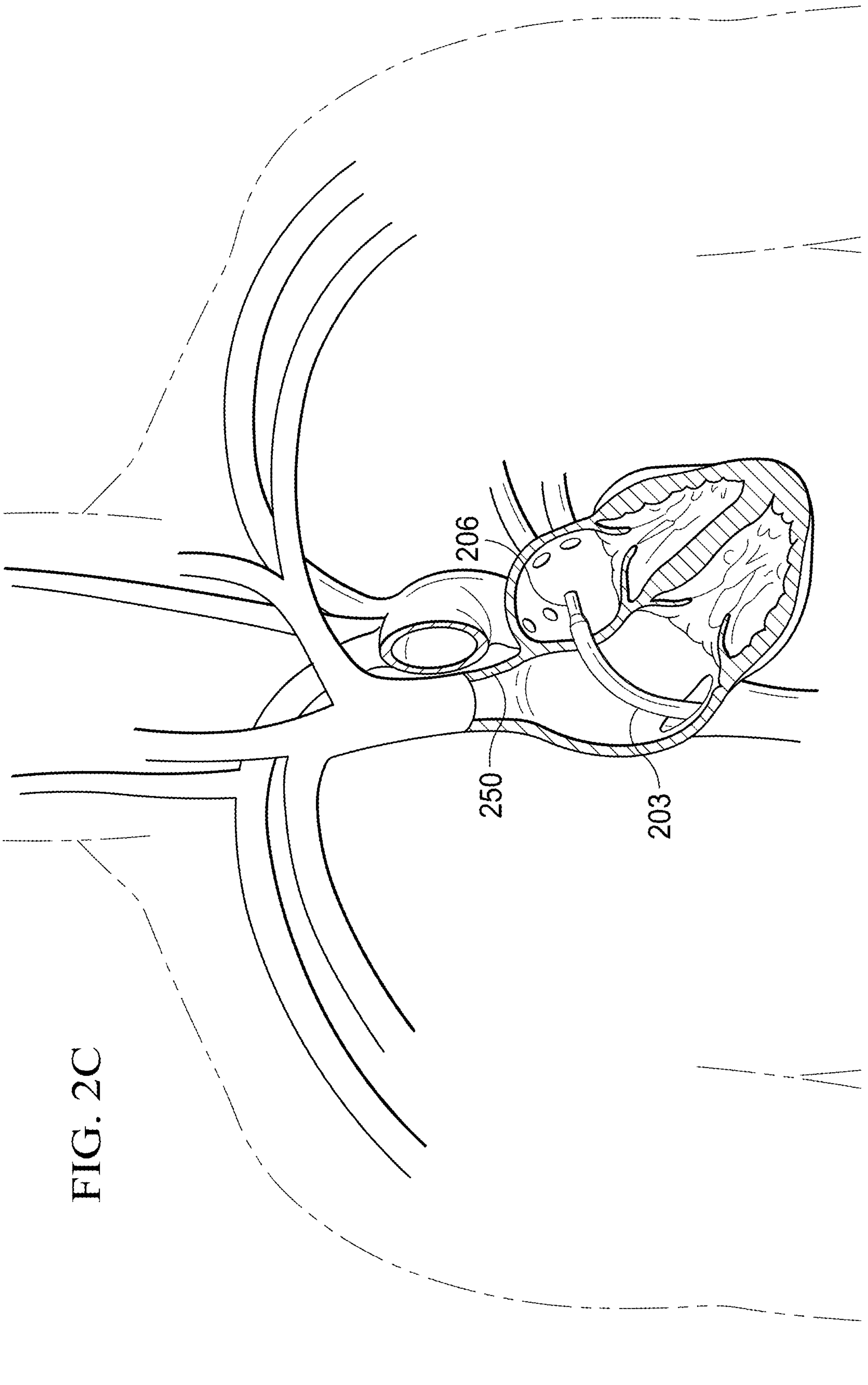
Figure 2D:
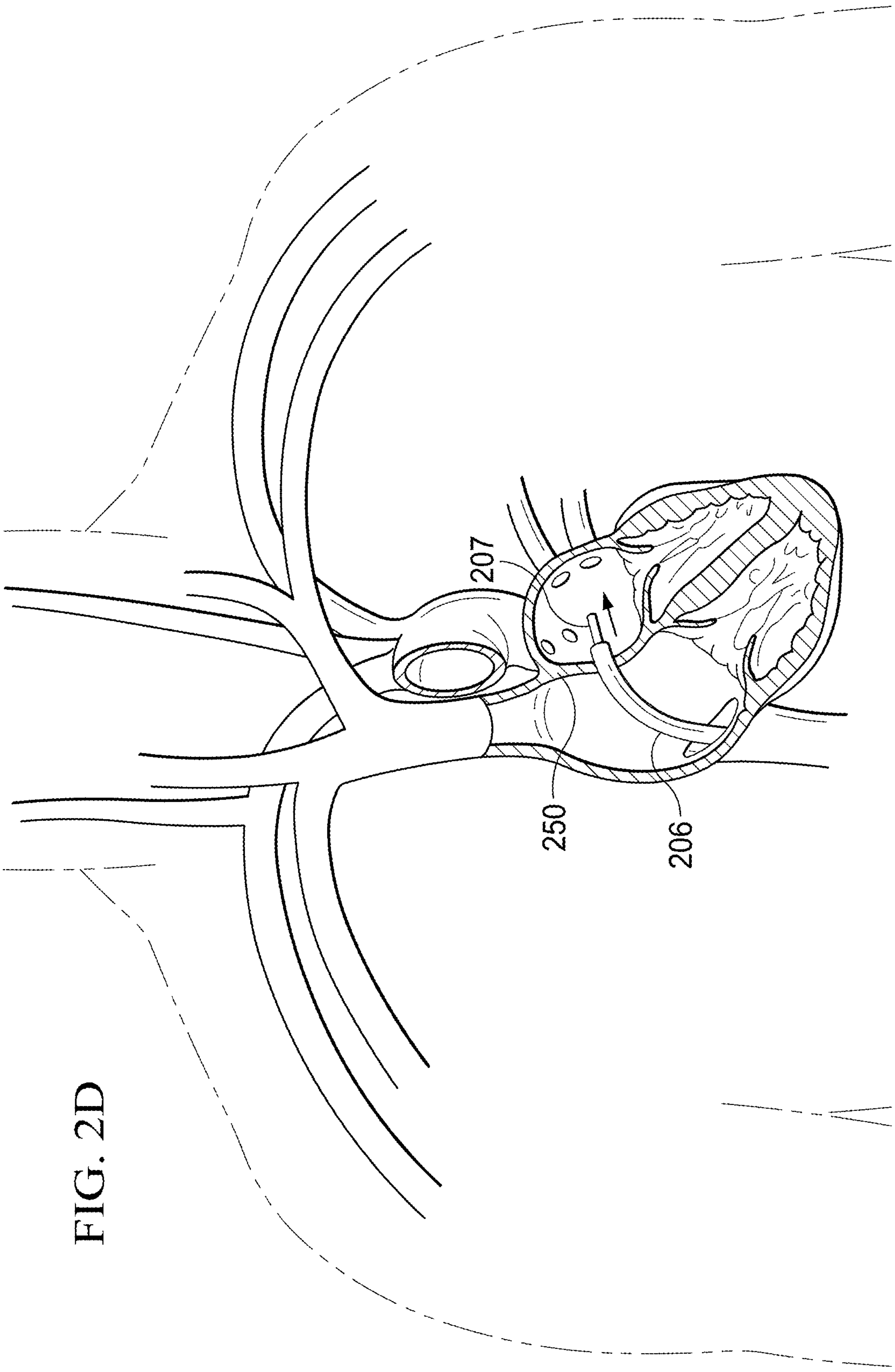
Figure 2E:
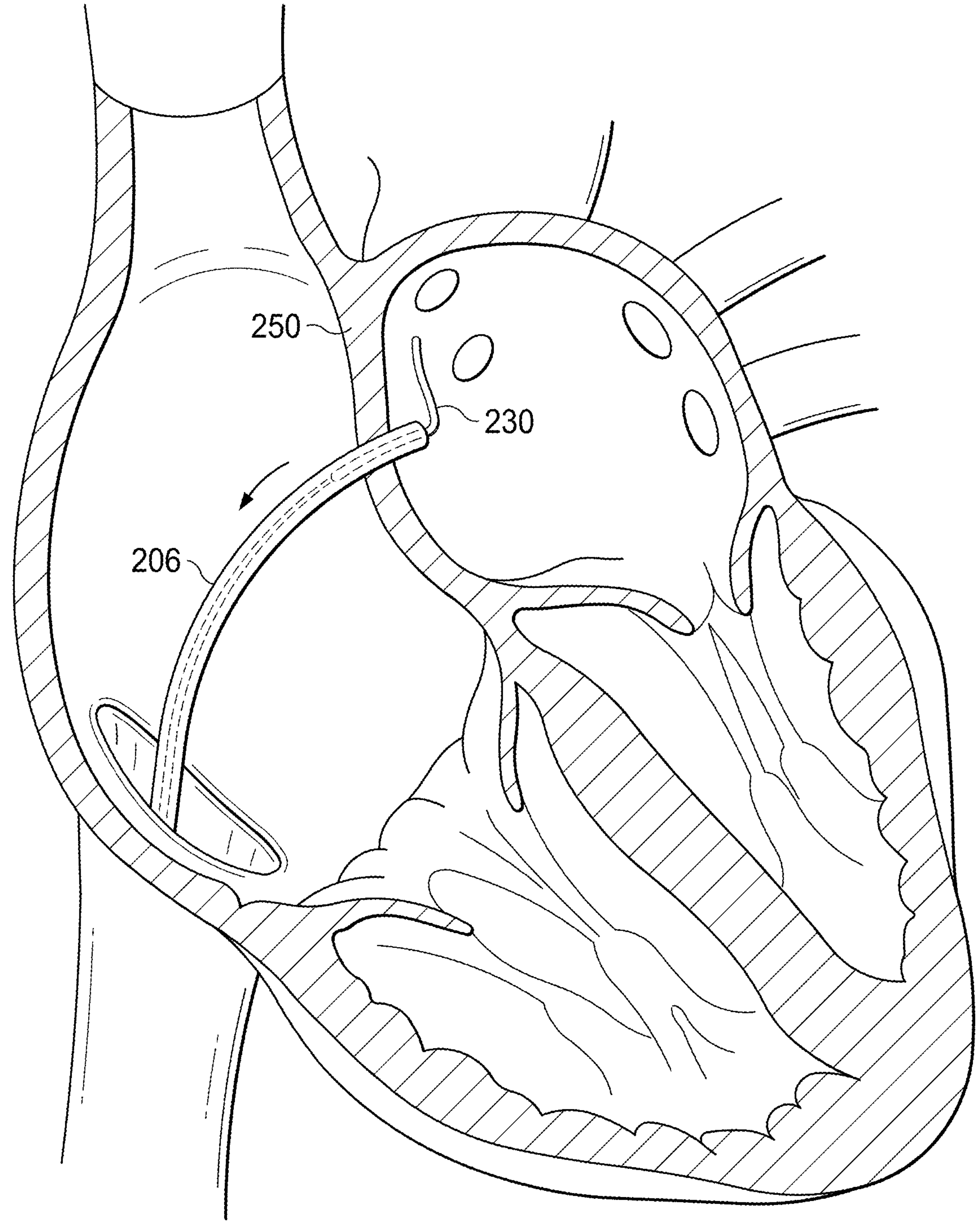

FIGS. 2A-21I illustrate a step-by-step procedure for attaching the leads to the heart. FIG. 2A depicts the initial transseptal puncture with a modified Seldinger technique. A guidewire 201 has been inserted via, for example, the groin and, through an obturator 202, into the left atrium. FIG. 2B depicts placing a transseptal sheath 203 through the transseptal puncture site 205 of the atrial septum 250. FIG. 2C depicts that the obturator 202 has been removed, and the transseptal sheath 203 remains in place with initial delivery of an anchor delivery sheath 206. The guidewire 201 has been removed. FIG. 2D depicts a septal electrode 230 (carrier or assembly) at the end of lead 103 exposed in the left atrium. The obturator 202 has been removed. FIG. 2E depicts the anchor delivery sheath 206 being retracted thereby exposing the septal electrode 230. The septal electrode 230 comprises a flexible elongate electrode. As can be seen, the distal region of the septal electrode 230 has a natural angled bend (approximately a right-angle bend) to it as shown.

Figure 2F:
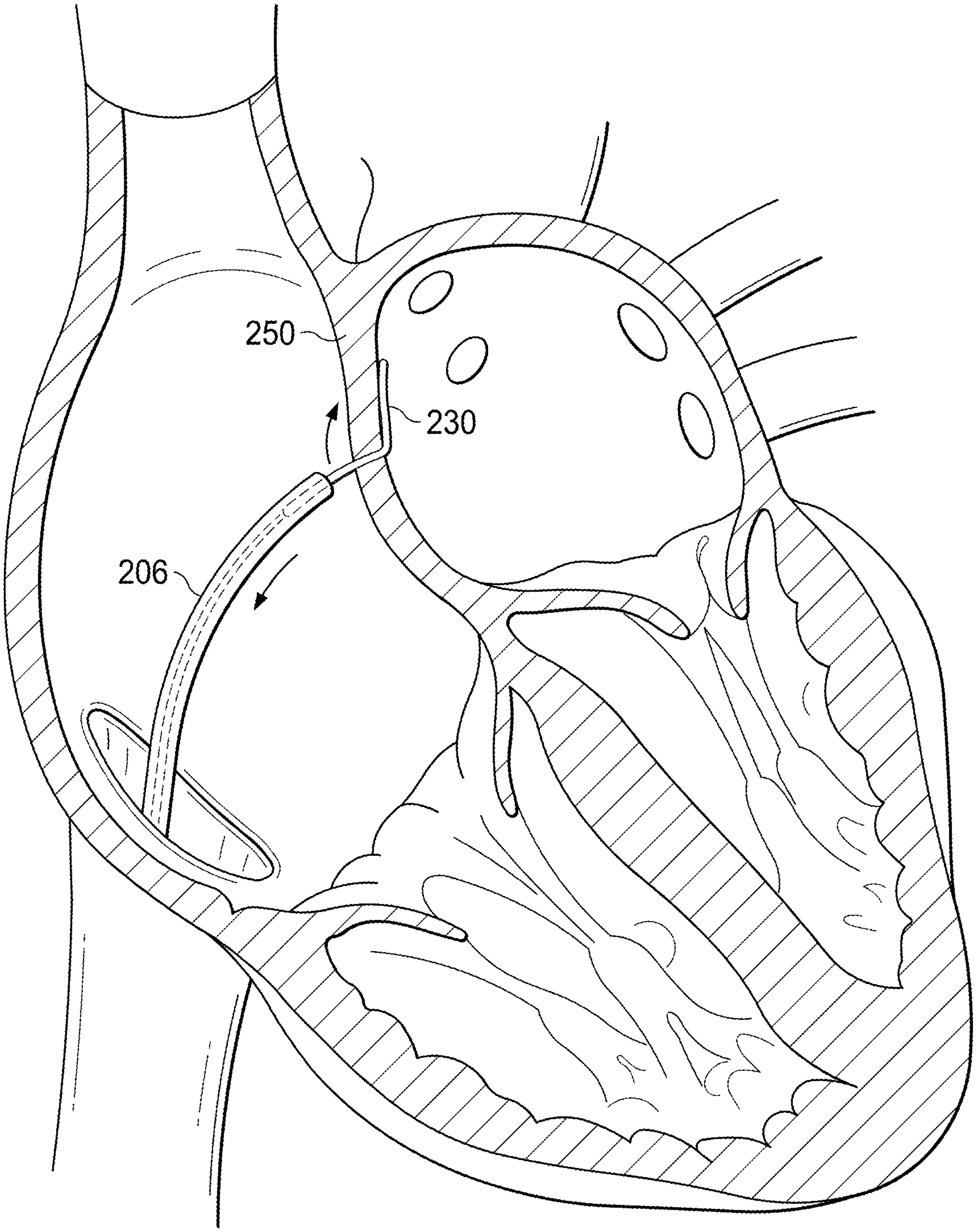

FIG. 2F depicts the further retraction of the anchor delivery sheath 206 and exposure of the septal electrode 230 against the atrial septum. The septal electrode 230 may comprise gold, nitinol or other suitable (e.g., inert and biocompatible) metal to transmit electricity to the heart. The septal electrode 230 maintains pressure against the atrial septum when deployed. The septal electrode 230 will maintain slight pressure on the septum to prevent movement of the device after it is deployed. As will be seen in the examples of FIG. 3A, the septal electrode 230 permits electrical current to flow to the septum 250 (and beyond) from an electronics enclosure.

Figure 2G:
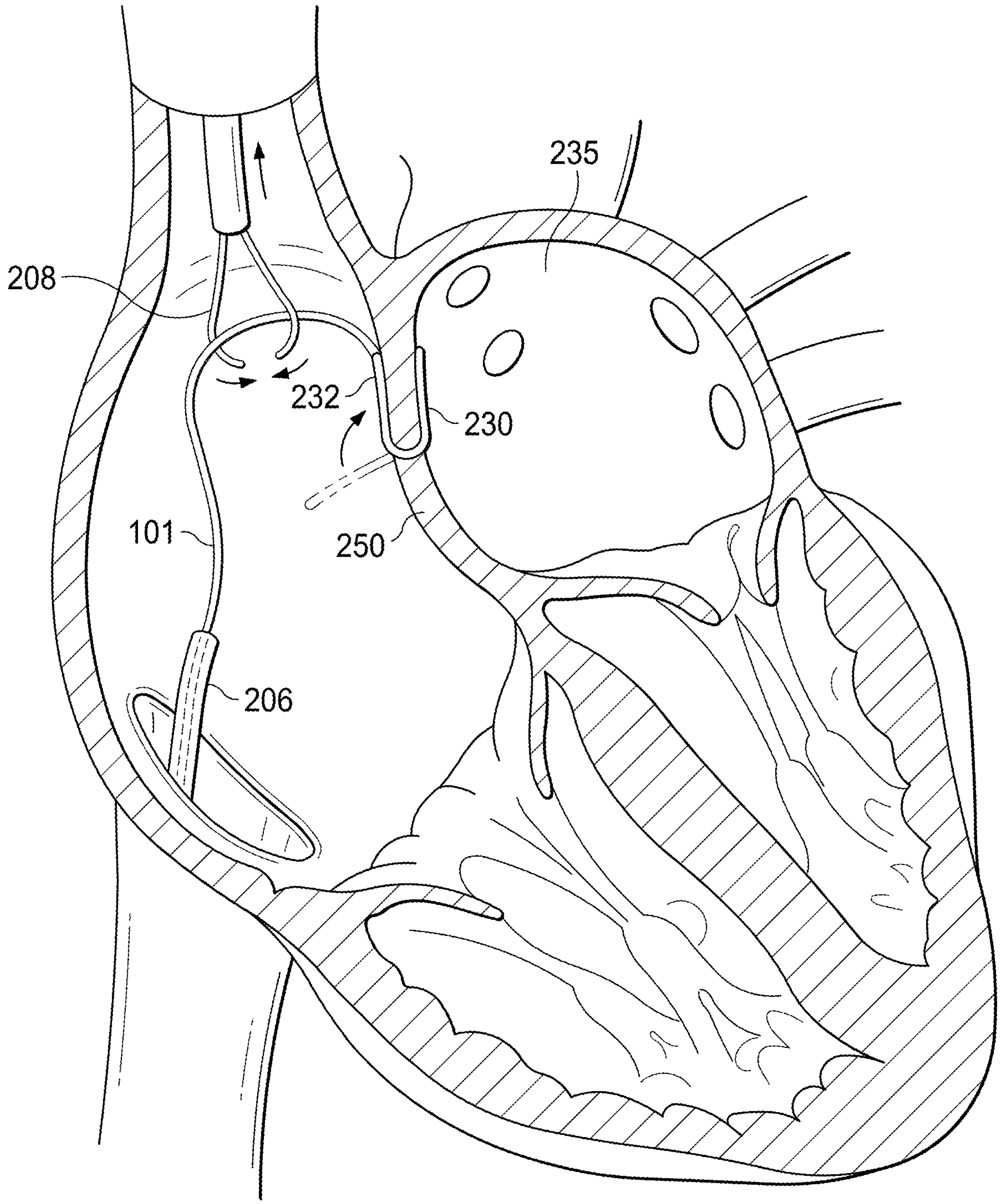

FIG. 2G depicts the septal electrode 230 fully deployed against the atrial septum 250. A snare device 208 is then depicted which allows the distal region of the lead to be moved from its insertion site (e.g., the groin) to the subclavian area or some other chest position at which the electronics enclosure is located. A portion 232 of the septal electrode 230 in the right atrium on the opposite side of the septum 250 from the portion of the septal electrode 230 in the left atrium is bent upward as shown using the snare device 208 thereby forming a U-shaped structure as shown. Because of the mechanical properties of the device (e.g., the memory shape structure), the wires will hug the endocardial surface. The septal electrode 230 may have configurations other than a U-shaped dip that perform the same or similar function as the U-shaped dip.

Figure 2H:
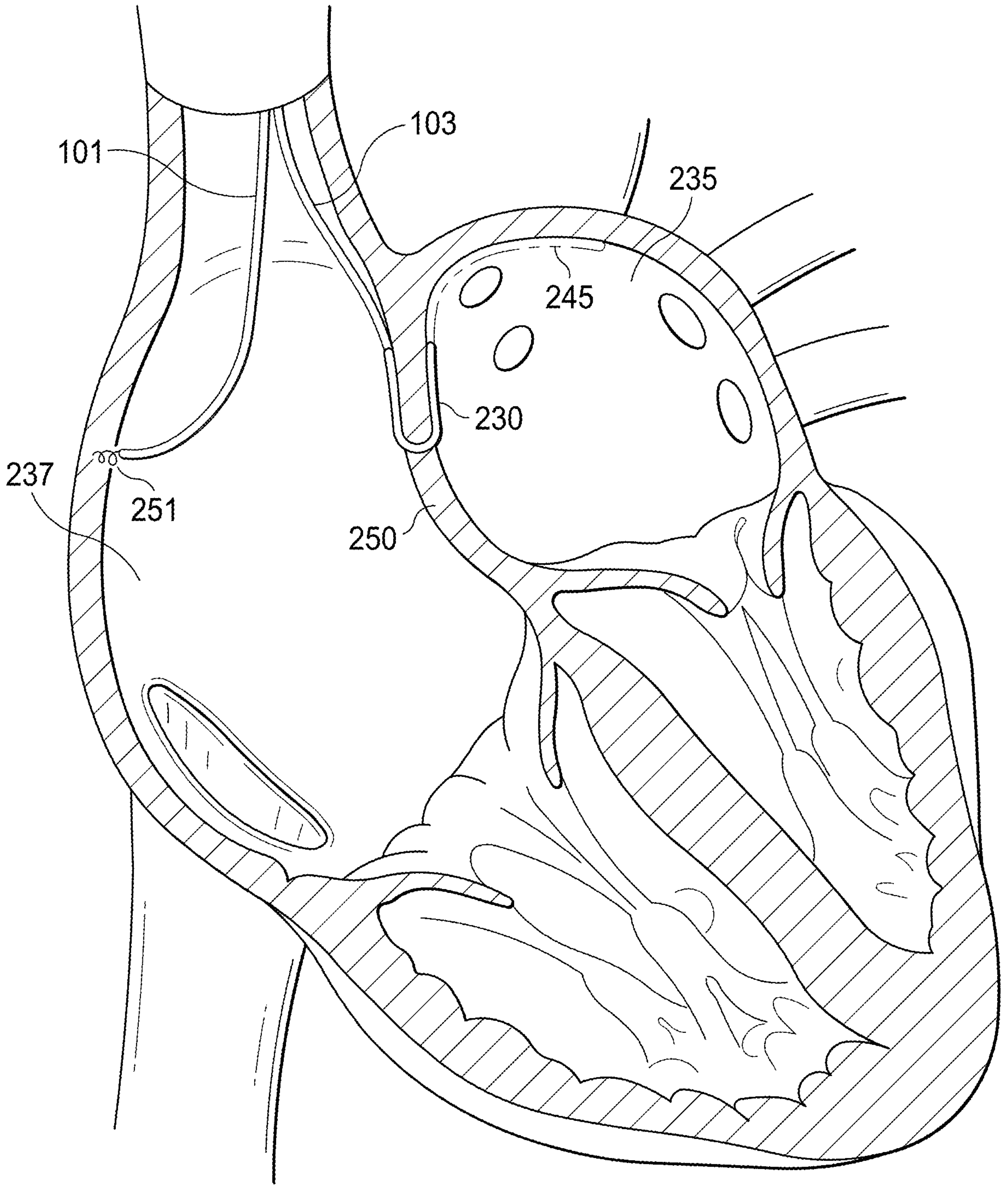

In other examples, the portion of the electrode pressed against the atrial septum in the left atrium may be longer than that shown in FIG. 2G or there be an additional array attached to the lead anchor 207 to increase the surface area along the atrial septum 250 and/or left atrium 235. For example, FIG. 2H depicts an extension 245L of the septal electrode 230 to increase the surface area for defibrillation of the left atria 235. Again, a shape memory metal (e.g., Nitinol) covering will hold the extensions tight against the atrial wall. Electrode 230 may be coated with a material such as gold to increase its conductivity. The curved wire can be made of nitinol or other shape memory material that can be straightened for implantation through a sheath into the patient-the curve shape can form inside the patient. The memory metal wire assembly can have the memory metal or similar material on the outside covering of the wire, as a part of the wire with insulation covering the wire or with any combination of a steroid, heparin coating or drug eluting coating. The device sits relatively flat against atrial wall (i.e., in continuous contact with the atrial wall such as the atrial septal wall) and eventually becomes strongly embedded in the cardiac tissue. This low profile discourages thrombus formation. The device has excellent electrical contact. The restraining device is held passively against the atrial septum. The restraining device easily attaching to the atrial septum with a low profile provides a safe route for deployment.

FIG. 2F also depicts both leads 101 and 103 exiting in the left subclavian area or other site on the chest. An electrode 251 is shown at the distal end of lead 101 and anchored into the right atrium 237.

FIGS. 2I-2M are illustrations of illustrative alternative embodiments of electrical contacts that may be used in conjunction with the septal electrode 230. FIG. 2I shows the septal electrode 230 with extension electrodes 245R and 245L (collectively 245) that extend from the septal electrode 230 in the respective right atrium 235 and left atrium 237, and are configured to maintain contact with the endocardium (i.e., inner walls) of the left and right atriums 235 and 237, respectively. The extension electrodes 245 may have reflectively identical shapes. Alternatively, the extensions electrodes 245 may have different shapes. However, in both cases, the extension electrodes 245 the exposed metal of the extension electrodes 245 may passively maintain contact with the walls of the left and right atria 235 and 237, respectively, by having a curved shape and formed of a shaped memory material that causes the extension electrodes 245 to press against the walls of the respective left and right atriums 235 and 237. As previously described, the extension electrodes 245 may be electrically connected to the septal electrode 230 or otherwise extend therefrom. The extension electrodes 245 may have the same or different lengths, and the lengths may be set based on an appropriate amount of resistance and electrical current transfer. Such lengths may be predetermined or may be established during installation if the septal electrode 230 is configured to enable length of the extension electrodes 245 to be adjustable prior to or during implantation. That is, the septal electrode 230 may allow for the extension electrodes 245 to be slidably connected to or detachable from/reattachable to the septal electrode 230, thereby allowing for an operator to alter length of the extension electrodes 245. In an alternative embodiment, devices including a septal electrode 230 with different length extension electrodes 245 may be available. Alternatively, an operator may cut the extension electrode(s) 245 depending on desired size and performance (e.g., smaller hearts may be suited with shorter extension electrodes 245). In an embodiment, the lead 103 may extend through and form an extension electrode 245 on a distal side of the lead and opposite side from where the lead 103 connects with the septal electrode 230, as additional shown and described herein.

With regard to FIG. 2I-A, in an embodiment, one or both of the extension electrodes 245 may include protrusions 246*a*-246*n* (collectively 246), such as in the shape of hooks, sawtooths, barbs, needles, or otherwise, that may be used to help maintain contact of the extension electrodes 245 with the walls of the left and right atria 235 and 237.

With regard to FIG. 2I-B, in an embodiment, rather than the extension electrodes (e.g., conductive metal), such as electrode 245L, being fully exposed, the electrodes may be partially exposed and partially insulated. For example, insulation 247 may extend on a side opposite the wall while an exposed electrode may be on the side of the wall, thereby the exposed electrode 245L may press against and extend along the endocardium of the wall. The insulation 247 may be impregnated polymer to inhibit thrombosis formation, for example. By maintaining insulation on the opposite side of the wall, reduced risk of a thrombus forming on the extension electrodes 245 may result. As previously described, a coating that reduces the risk of clotting may be applied to the insulation to avoid thrombus formation on the electrodes and wires. And, because an extended length of exposed electrode contacts the endocardium, it may be possible to provide lower energy and/or different signaling to the heart for pace or other treatments, thereby enabling a patient to perform treatments on themselves without risk of conventional treatments that typically requires a patient to be within a medical facility.

Figure 2J:
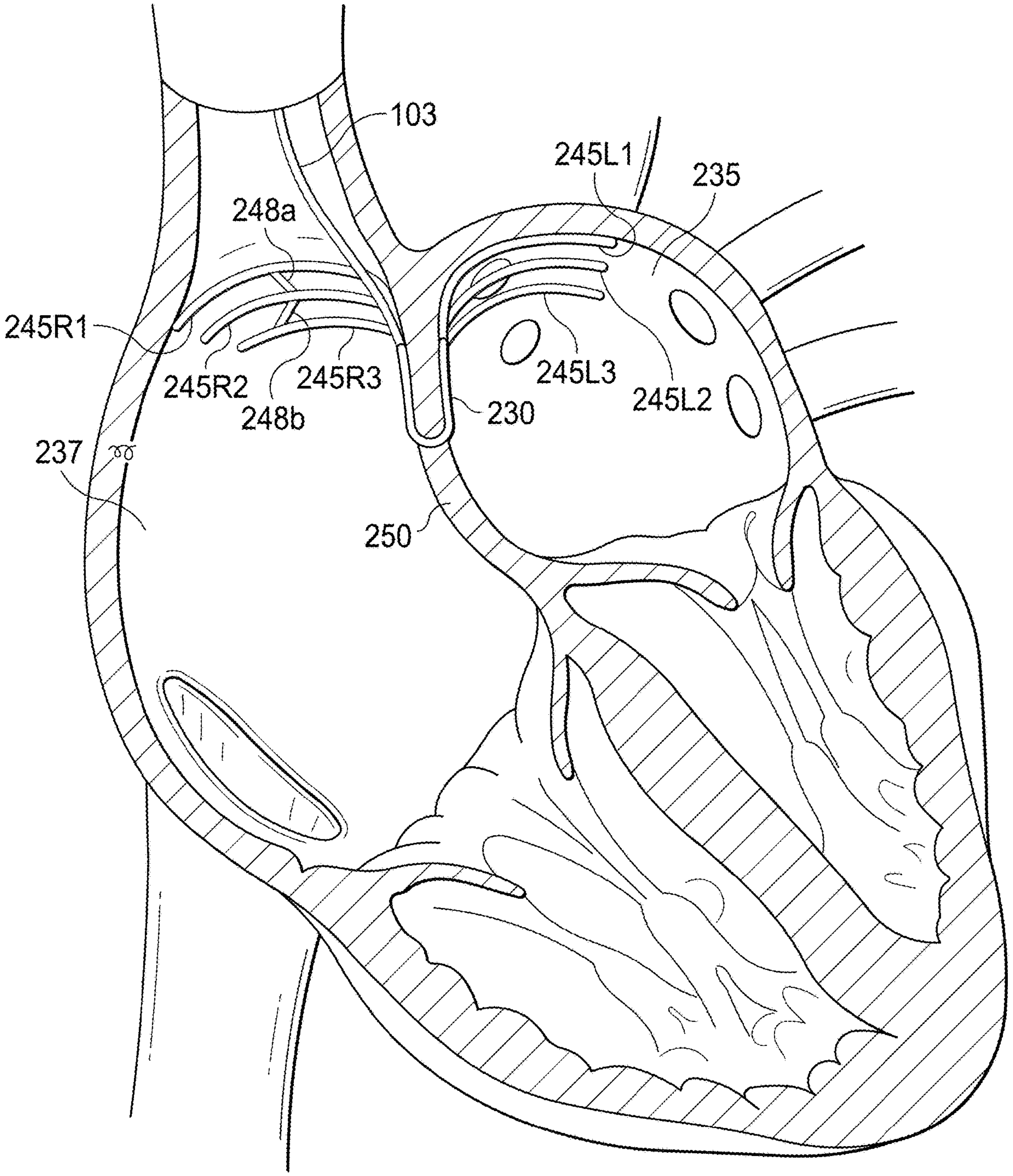

With regard to FIG. 2J, an illustration of an alternative configuration of extension electrodes is shown to include a plurality of extension electrodes 245L1-245L3 (collectively 245L) positioned in the left atrium 235 and extension electrodes 245R1-245R3 (collectively 245R) in the right atrium 237. In this embodiment, there are three extension electrodes 245L and three extension electrodes 245R in each of the left and right atria 235 and 237. It should be understood, however, that alternative numbers, such as two or more extension electrodes, may be positioned in each of the left and right atria 235 and 237. Moreover, it should be understood that a different number of extension electrodes may be positioned in each of the left and right atria 235 and 237. As with the extension electrodes 245 of FIG. 2I, the extension electrodes 245L and 245R may be electrically connected or otherwise extend from the septal electrode 230. The thicknesses and configuration of the extension electrodes 245L and 245R may be such that the collective electrodes 245L and 245R may be deployable via a transseptal sheath, as previously shown with regard to FIG. 2C, for example. The extension electrodes 245 may be part of a lead (e.g., lead 103) or independent of a lead. Lengths of the respective extension electrodes 245 may vary depending on patient, treatment, and use of the extension electrodes 245.

The extension electrodes 245L and 245R may have the same or similar physical characteristics as previously described with regard to the extension electrodes 245 of FIG. 2I, for example (e.g., gold, nitinol, inert and biocompatible metal, preformed shape, etc.). The extension electrodes 245L and 245R may further have optional connection features 248*a* and 248*b* (collectively 248) between adjacent electrodes (e.g., 245R1-245R2, 245R2-245R3) so that the adjacent electrodes have a maximum restrained spacing between one another. Although not shown, the extension electrodes 245L in the left atrium 235 may also have connection features that are the same or similar to the connection features 248. In an embodiment, the connection features 248 may be electrical conductors or non-electrical conductors and may also be formed of the same or similar material as the extension electrodes 245. Moreover, the connection features 248 may be shaped to assist with maintaining the extension electrodes 245L and 245R against the walls of the left and right atria 235 and 237. It should be understood that the configuration may be leadless, as further provided herein.

Figure 2K:
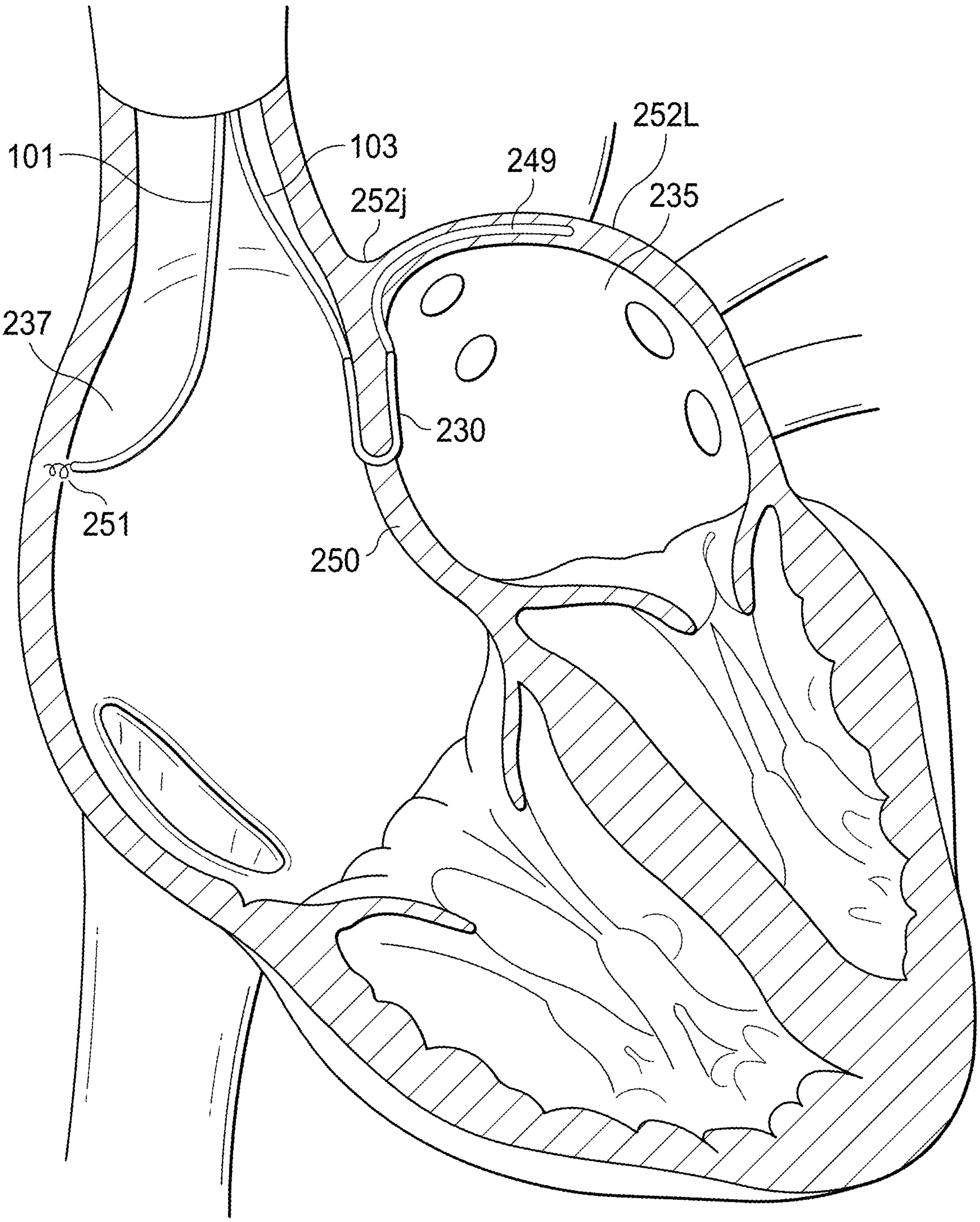

With regard to FIG. 2K, an illustration of an alternative illustrative embodiment of extension electrode(s) is shown, In this embodiment, an extension electrode 249 is shown to be intramural (i.e., be extended through and remain within a wall 252L). As with the extension electrode 245L of FIG. 2I, the extension electrode 249 may be electrically connected to or otherwise extend from the septal electrode 230 that is held to the atrial septum 250. Both leads 101 and 103 are shown to be exiting in the left subclavian area or other site on the chest. An electrode 251 is shown at the distal end of lead 101 and anchored into the right atrium 237. It should be understood that the lead 101 and electrode 251 may not be utilized if an extension electrode, such as extension electrode 245R, is disposed in the right atrium 237, as provided in FIG. 2I.

In an embodiment, the extension electrode 249 may be inserted into the wall 252L at a wall junction 252*j* between the left and right atria 235 and 237, as the wall junction 252*j* is slightly thicker than the wall 252L, thereby being slightly safer than entering directly into wall 252L. In one embodiment, the extension electrode 249 may extend through the epicardium of the wall 252L, but remain inside the pericardium of the wall, and the pericardium may hold the extension electrode 249 against the epicardium to apply electrical signals applied to the extension electrode 294 to the epicardium of the left atrium 235. In an embodiment, the extension electrode 249 may be fully non-insulated. Alternatively, an insulator may extend along the extension electrode 249 to an approximate distance of where the wall 252L extends from the wall junction 252*j*, thereby limiting electrical signals to the left atrium 235. Alternative configurations of the extension electrode 249 and insulation thereon are possible.

Figures 1, 2L:
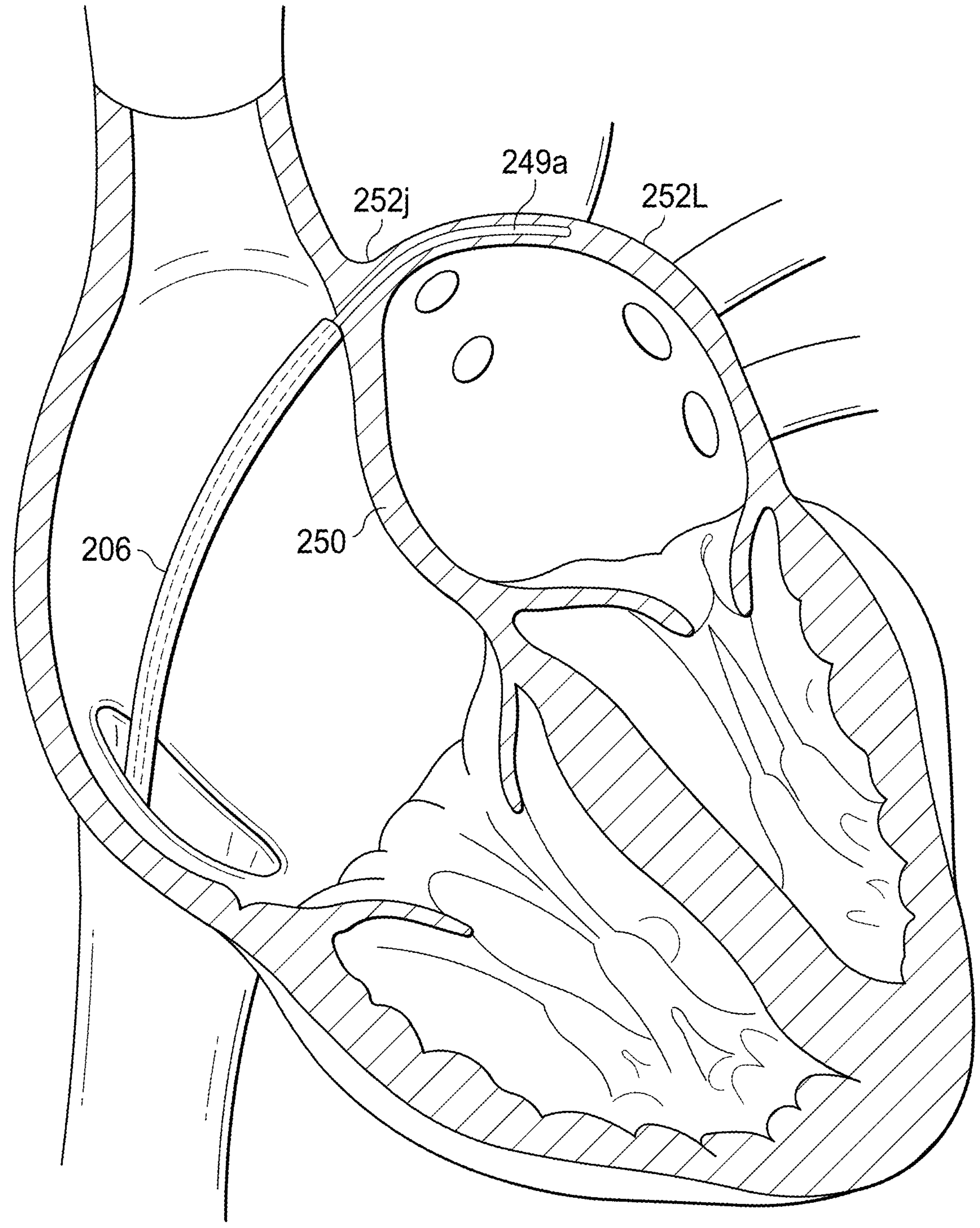
Figures 2, 2L:
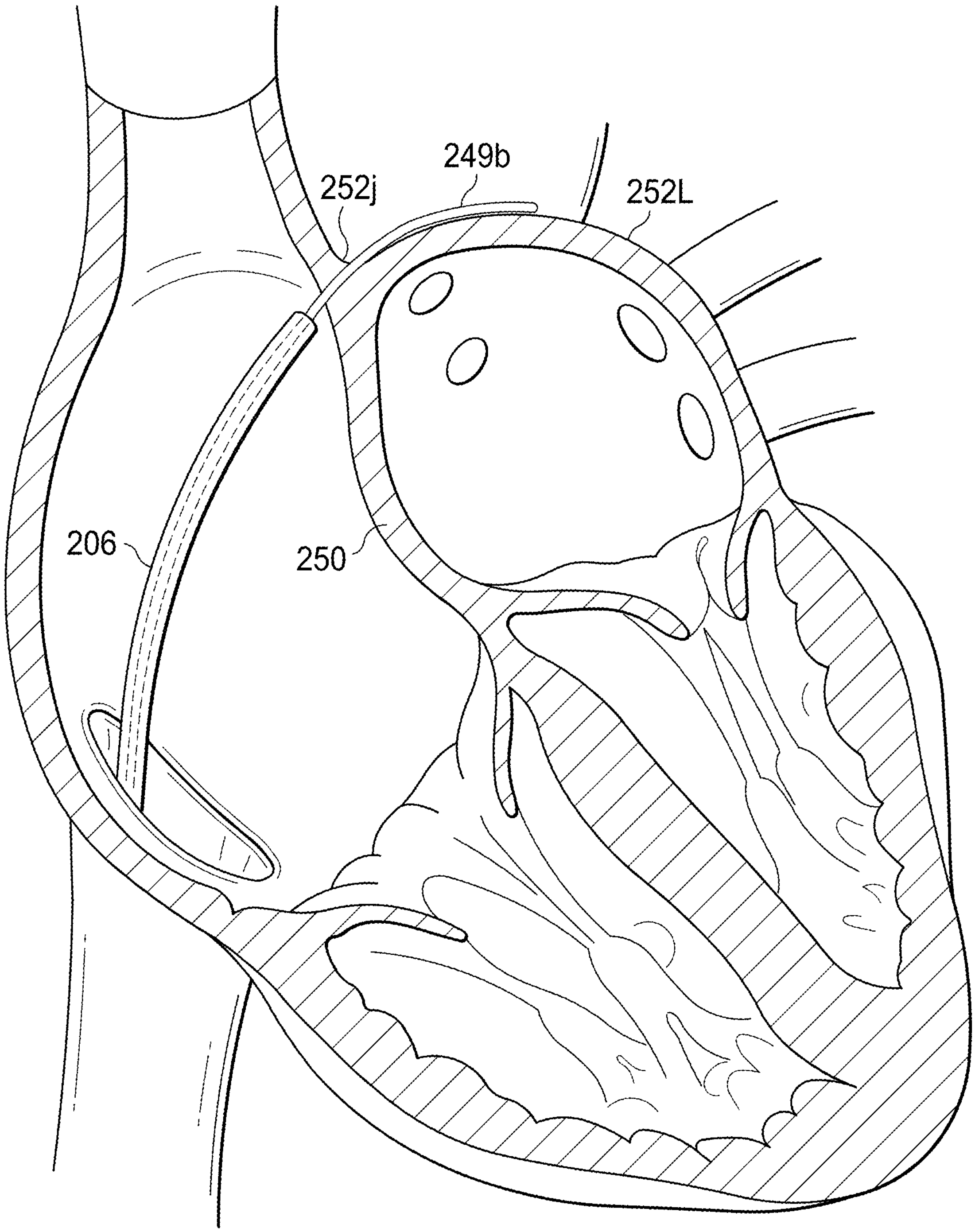
Figure 2M:
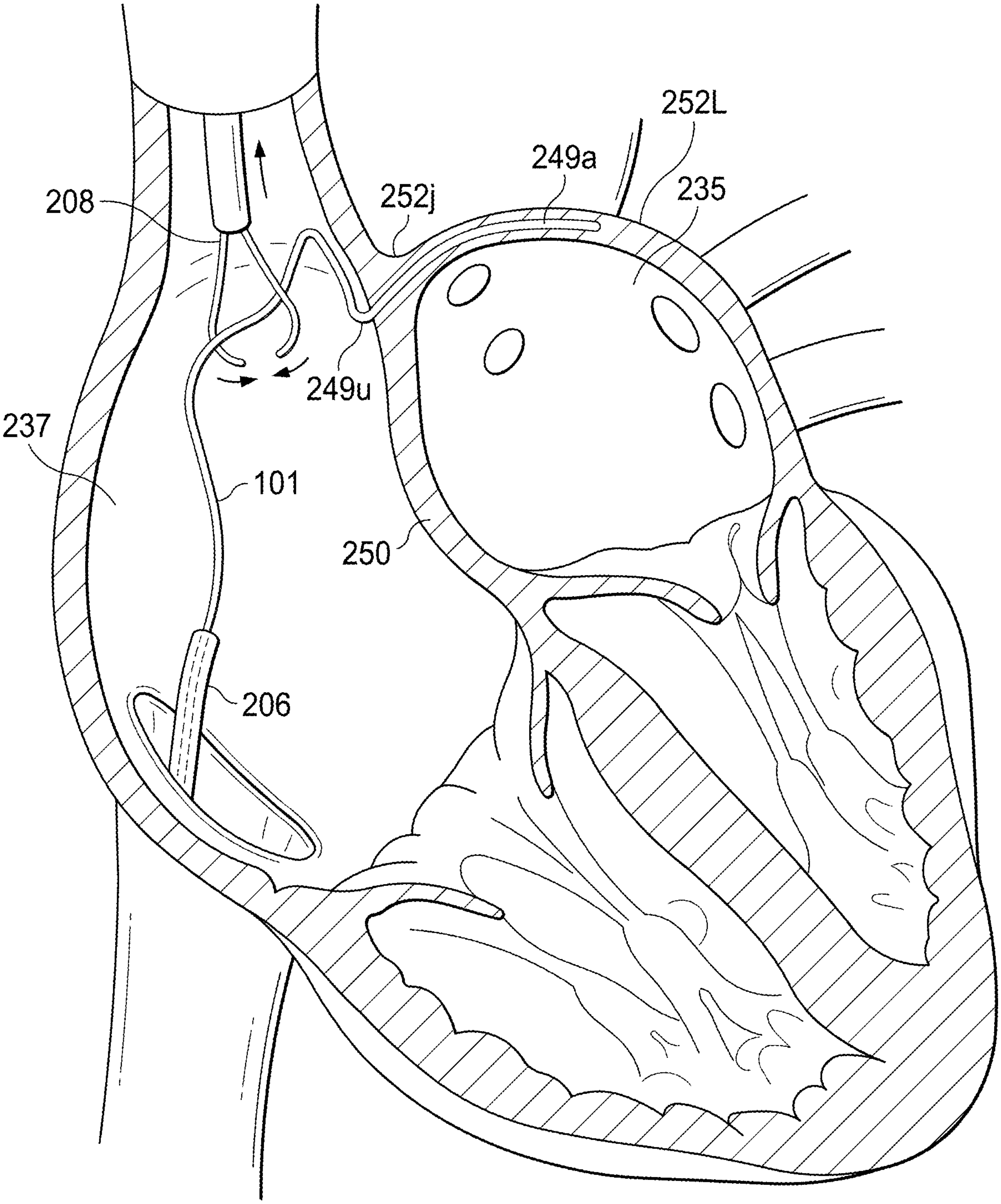

With regard to FIGS. 2L-1, 2L-2, and 2M, an illustrative sub-process for inserting an alternative configuration of an extension electrode 249*a* using the anchor delivery sheath 206 of FIG. 2E is shown. However, rather than entering through a center portion of the septum 250, the extension electrode 249*a* may enter through the wall junction 252*j* at the top of the septum 250 from the right atrium 237, thereby simplifying the insertion process into the wall 252L of the left atrium 235. As shown in FIG. 2M, the extension electrode 249*a* may have a u-curve 249*u* that forms a curved bend to cause the extension electrode 249*a* to extend along a wall of the right atrium 237. The u-curve 249*u* may be preset such that when the extension electrode 249*a* is released from the sheath, the u-curve 249*u* is automatically shaped. In an embodiment, to secure the extension electrode 249*a* in the wall of the left atrium 235, a number of different techniques may be utilized, including a septal electrode that may be curved or appear as a straight stud with a retention feature that secures to the septum 250, post, suture, or any other mechanism that may assist in maintaining the maintaining the position of the extension electrode 249*a*. In another embodiment, the extension electrode 249 may include a protrusion anywhere along the length or at the u-curve 249*u* that may prevent the extension electrode 249*a* from backing out of the wall 252L and wall junction 252*j*.

In the event that the lead 101 is to extend to a device, then other procedural processes as previously described may be utilized. In an embodiment, to support the u-curve 249*u* and curve of the extension electrode 249*a* that extends intramural through the wall 252L of the left atrium 235, those portions (i.e., u-curve 249*u* and extension electrode 249*a*) may be formed of material with shape memory, as previously described. Because the extension electrode 249*a* extends intramural, there is minimal or no ability for any clotting to occur in the left atrium 235 because the extension electrode 249*a* does not enter the left atrium 235. Moreover, if the extension electrode 249*a* is secured to the wall of the right atrium 237 without having to pierce the septum 250, other procedural and operational risks may be reduced.

With regard to FIG. 2L-2, another illustrative sub-process for inserting an alternative configuration of an extension electrode 249*b* using the anchor delivery sheath 206 of FIG. 2E is shown. In this process, rather than the extension electrode 249*b* extending into the myocardium and being intramural, the extension electrode **249*b* may extend through the wall junction 252*j* and along the epicardium of the wall 252L. Extending through the wall junction 252*j* that is thicker than the thinner walls or atrial septum 250, a reduced risk of tear or bleeding is possible. Although only one extension electrode 249*b* is shown, it should be understood that multiple extension electrodes 249*b* may be utilized and extend along the epicardium of the wall 252L. In an embodiment, to limit the ability for bleeding to occur through a hole formed by the extension electrode 249*b* from the right atrium to outside the wall 252L, a hemostatic agent or tissue adhesive may be used to seal the opening through which the extension electrode 249*b* extends. In an embodiment, the hemostatic agent may be disposed or pre-applied on the extension electrode 249*b* such that the hemostatic agent is automatically applied when inserted into the wall junction 252*j*, thereby limiting or preventing blood to flow through the wall junction 252*j* external the wall 252L. Other mechanical, chemical, and/or biological techniques may be utilized to limit or prevent blood flow from the opening created by the extension electrode 249*b***.

Figure 2N:
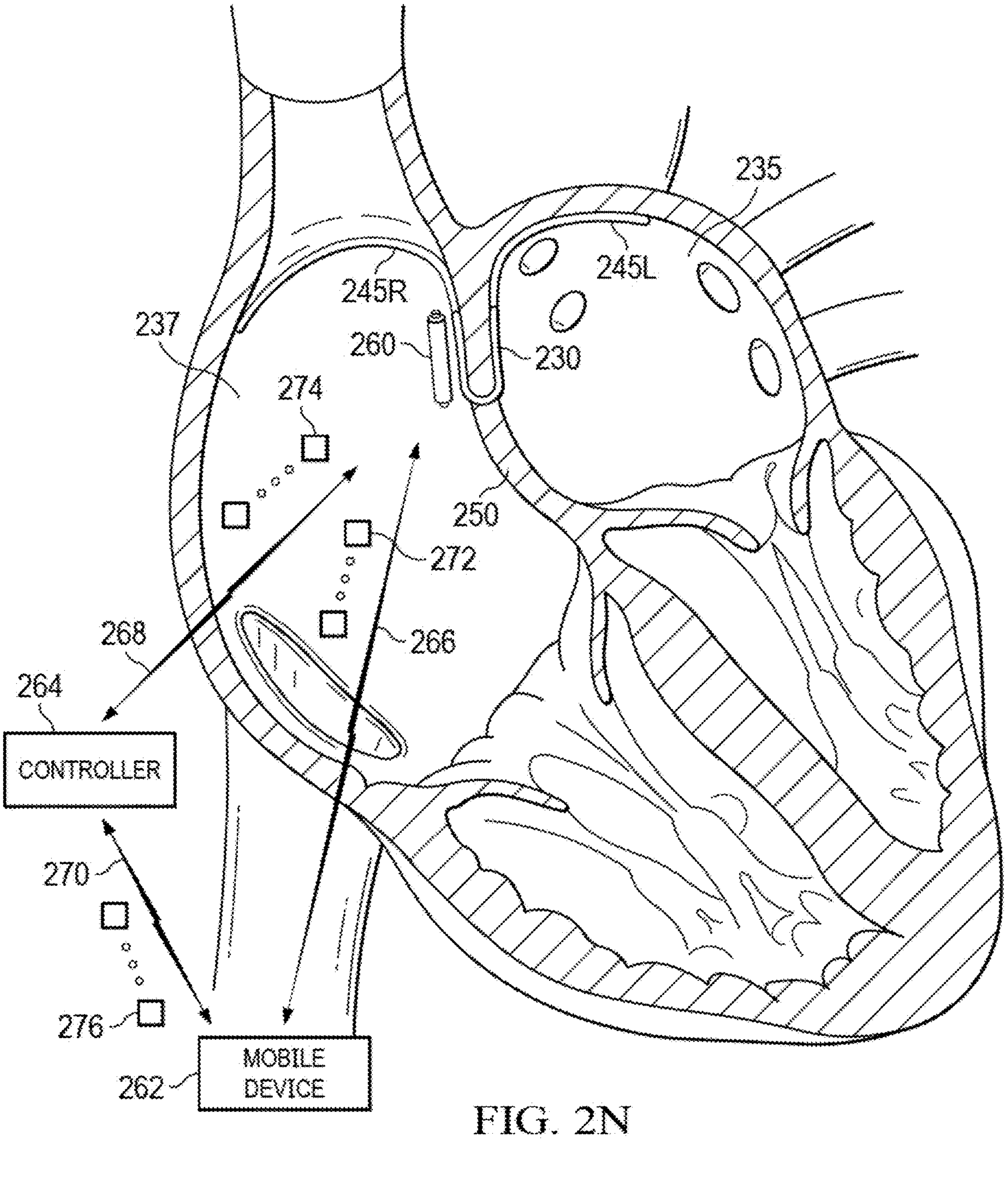
FIGS. 2N and 2O are embodiments of illustrative leadless pacemakers that are attached to illustrative septal electrodes having electrical contacts extending therefrom.

FIG. 2N is an illustration of an illustrative leadless pacemaker 260 that is attached to an illustrative septal electrode 230 having electrical electrodes 245R and 245L (collectively 245) extending therefrom. In this embodiment, the leadless pacemaker 260 may be elongated and extend along the septal electrode 230, and may be in electrical contact therewith such that any electrical signals produced by the leadless pacemaker 260, those signals may be transferred to the septal electrode 230, which causes the electrical signals to extend along the extension electrodes 245. It should be understood that if only the extension electrode 245L extends from the septal electrode 230, then the electrical signals may be extended into the left atrium 235 and along the endocardium of the wall of the left atrium 235. The septal electrode 230 and leadless pacemaker 260 may be connected to one another in a variety of different ways, but is to be physically connected in a manner that has no adverse interaction to a patient's heart or health. In an embodiment, a housing of the leadless pacemaker 260 may have the septal electrode 230 being integrated with one another (e.g., monolithic single piece of material) during production. Alternatively, the two elements 230 and 260 may be connected to one another using attachment elements, such as screws, bolts, clips, structural linking elements, etc. Moreover, because the leadless pacemaker 260 does not need to have electrodes extend from the heart to an implanted device (e.g., controller), then no leads are necessary to extend from the leadless pacemaker 260 or septal electrode 230.

As further shown, a mobile device 262, such as a smartphone or other portable electronic device, and controller 264, which may also be an electronic device that may be attached to or wirelessly in communication with the mobile device 262. Wireless communications channels 266, 268, and 270 may enable wireless communications between the leadless pacemaker 260 and mobile device 262, leadless pacemaker 260 and controller 264, and mobile device 262 and controller 264. Data 272, 274, and 276 may be communicated via the respective communications channels 266, 268, and 270 and between the respective devices configured to communicate via the communications channels 266, 268, and 270. The communications channels 266, 268, and 270 may be local communications channels using local wireless communications protocols (e.g., Bluetooth®, WiFi®, or otherwise). Each of the mobile device 262 and controller 264 may include a processor, memory, and wireless communications devices to support operations of the leadless pacemaker 260. The processors of the mobile device 262 and controller 264 may be configured to process and send data and/or control signals between one another and with the leadless pacemaker 260.

In operation, the leadless pacemaker 260 may sense signals and/or operations of the heart (e.g., heartbeat rate in either or both of the left atrium 235 and right atrium 237) via data signals 272 via the communications channel 266 to the mobile device 262. The mobile device 262 may be configured to receive and display data (e.g., graphics, text, text and graphics) for a user of the mobile device 262. In an embodiment, a mobile app (not shown) may be configured to receive and process the data signals communicated by the leadless pacemaker 260. The mobile app may further be configured to cause the mobile device 262 to communicate with the controller 264 via the communications path 270 by sending data signals 276 that may, in turn, cause the controller 264 executing software on a processor, to send control signals to the leadless pacemaker 260 for controlling pace, for example, of one or both the left and right atria 235 and 237, respectively. It should be understood that the same or similar configuration may be utilized in the left and right ventricles of the heart.

The leadless apparatus could wirelessly communicate with a phone or other device that may deliver specific electrical energy in specific configurations that could terminate the firing of an abnormal atrial focus or foci with or without a defibrillation. This leadless apparatus could also be configured in the leadless device itself. The recording and storing of information from the atrial walls or other areas of the heart may be stored and analyzed in the device itself or the information could be sent to other devices, which may analyze the information to guide further therapy.

Because the extension electrodes 245 are disposed within the respective left and right atria 235 and 237, the same or different pace or other signals may be applied as is conventionally applied. In other words, because the extension electrodes 245 are maintained against the endocardium, lower power signals (e.g., less than 1 joule) may be applied by the leadless pacemaker to cause the heart to be properly paced or otherwise treated. It should be understood that similar low amounts of energy may be applied to the extension electrodes extending from the septal electrode 230 if a lead is used to connect thereto (see, for example, FIG. 2I). It should be understood that the leadless pacemaker 260 may be configured with an energy source sufficient to operate for many years. Alternatively, sufficient wireless energy may be transferred to the leadless pacemaker 260 from the controller 264, for example, to enable the wireless pacemaker 260 to perform necessary functions (e.g., applying pacing signals).

Because of the low amount of power to be applied to the heart because of the configuration of the extension electrode (s) 245, a patient may self-administer treatment via the mobile device 262 and/or controller 264. Software executed by the mobile device 262 may enable the user to monitor his or her heart using a mobile app, which may notify the user of a rhythmic abnormality, for example. The patient may sit or lay down before self-administering treatment, thereby being safe. Because of the lower energy, the patient may feel no or minimal discomfort. If the software is configured to ramp up electrical signaling and receive feedback after each signaling is applied, for example, the process may perform treatments with minimal interaction by the patient or risk to the patient.

Figure 2O:
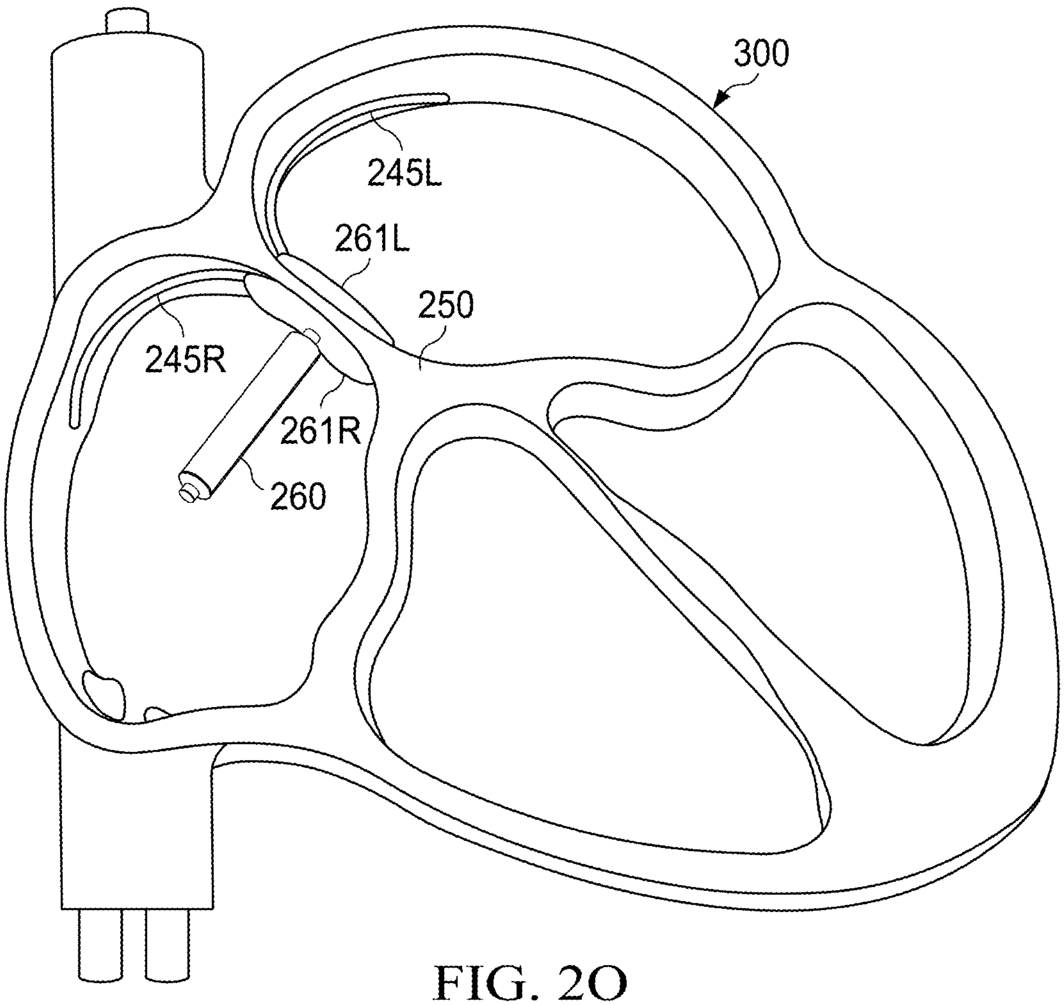

With regard to FIG. 2O, the leadless pacemaker 260 may be connected to the atrial septum 250 using an alternative septal electrode element 261R, which connects to a septal electrode element 261L to form a septal electrode 261. The septal electrode 261 may be the same or similar to the septal electrode 400 (FIG. 3C) and provide the same or similar electrical and mechanical functions as the septal electrode 400, as further described herein. In this embodiment, the leadless pacemaker 260 may extend perpendicularly from the septal electrode element 261R, but may also be configured to extend along a wall or be integrated with the septal electrode element 261R. Still yet, the leadless pacemaker 260 may be connected to or be integrated with the septal electrode element 261L. In either case, an electrical connection is made between the leadless pacemaker 260 and septal electrode element(s) 261R and 261L so as to provide the various electrical stimulation support to the heart of the patient. Rather than simply applying electrical connection from the septal electrode 261, extension electrodes 245R and 245L may extend along the endocardium of the left and right atria 235 and 237. It should be understood that alternative configurations of the extension electrodes 245 may be utilized, as further described herein. In an embodiment, the septal electrode elements 261 may be configured without the ability to make electrical connections with the endocardium at the atrial septum, but rather simply support the extension electrodes 245 and enable electrical communications between the leadless pacemaker 260 and extension electrodes 245.

Figure 3A:
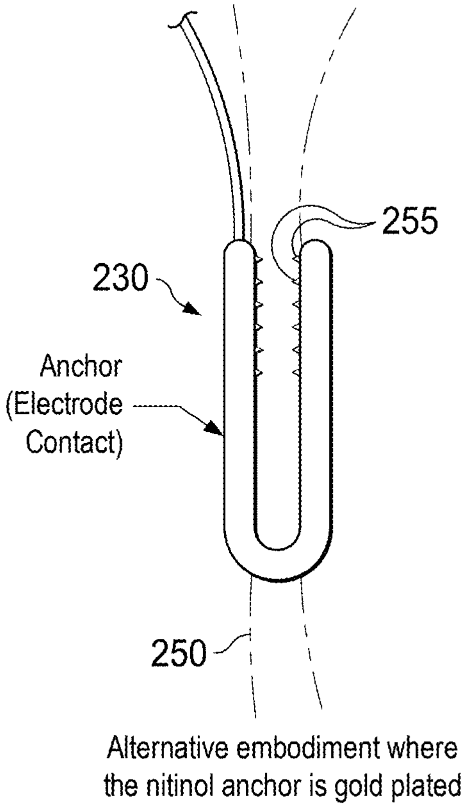
FIG. 3A shows a dose-up view of one example of the septal electrode which includes protrusions to help hold the septal electrode in place against the septum.
Figure 3B:
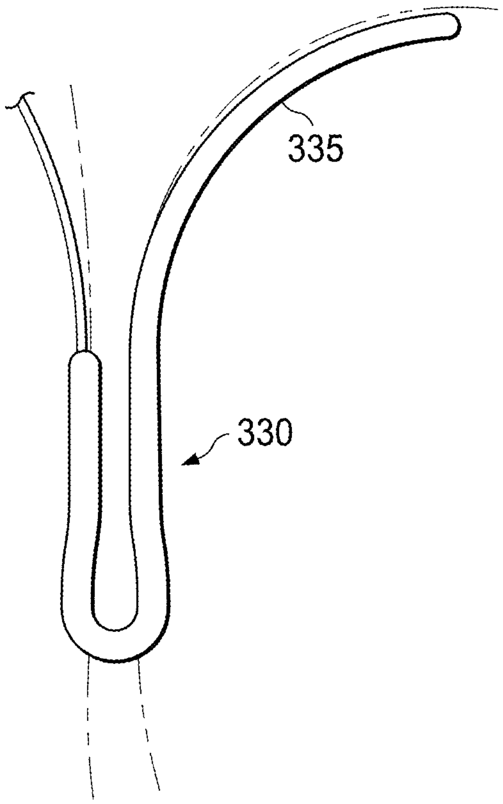
FIG. 3B shows another example of a septal electrode with extension further into the left atrium, again with the wires and electrode flush against the endocardium.
Figure 3C:
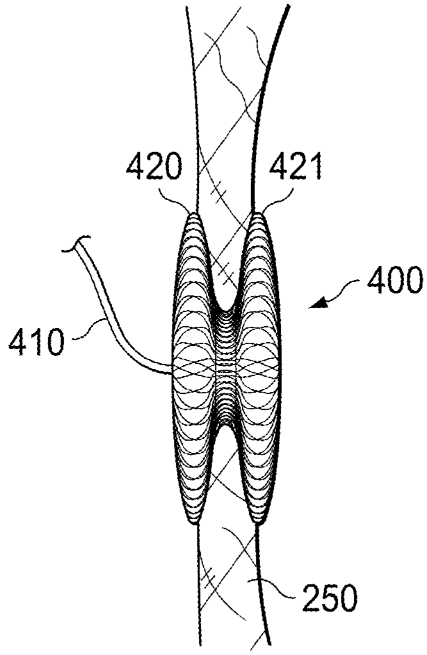
FIG. 3C shows yet another example of a septal electrode with deployable wings held in place by the device against the atrial wall.

FIGS. 3A-3C depict examples of devices that specifically allow for atrial defibrillation with two electrodes. One of the electrodes is placed in the right atrium (e.g., electrode 251 shown in FIG. 2H), but other locations are possible as well such as the right ventricle, left ventricle, or coronary sinus. The other electrode comprises the septal electrode 230 that sits along the atrial septum. FIG. 3A depicts a septal electrode 230 hugging both sides of the atrial septum 250. Protrusions 255 (e.g., teeth) extend towards and slightly into the septum 250 and allow secure positioning along the septal wall to help anchor the septal electrode 230 in place on opposite sides of the septum 250.

FIG. 3B is similar to FIG. 2H and depicts a septal electrode 330 hugging the atrial septum with a left atrial (could also be right) extension 335 for additional surface area (compared to septal electrode 230 in FIG. 3A) for defibrillation. Protrusions 255 may be included in this embodiment as well to help hold septal electrode 330 and its extension 335 in place.

FIG. 3C depicts an alternate septal electrode 400 which covers both sides of the atrial septum 250. Septal electrode 400 comprises a plug having an electrode array. The plug can have electrode properties, or the plug may incorporate electrode(s) with sufficient conductivity, such as gold plating. The extra electrode(s) can be weaved into the plug, or can be a circular electrode on one or both sides of the device, or can be more than one electrode in circles about the circumference or radius or in between the plug. The extra electrode is attached to a wire 410 which exits the heart in the same manner as the device in FIGS. 3A and 3B. Opposing wings 420 and 430 can be deployed (e.g., fan out) to anchor the device against the septum 250 as shown.

Figure 3D:
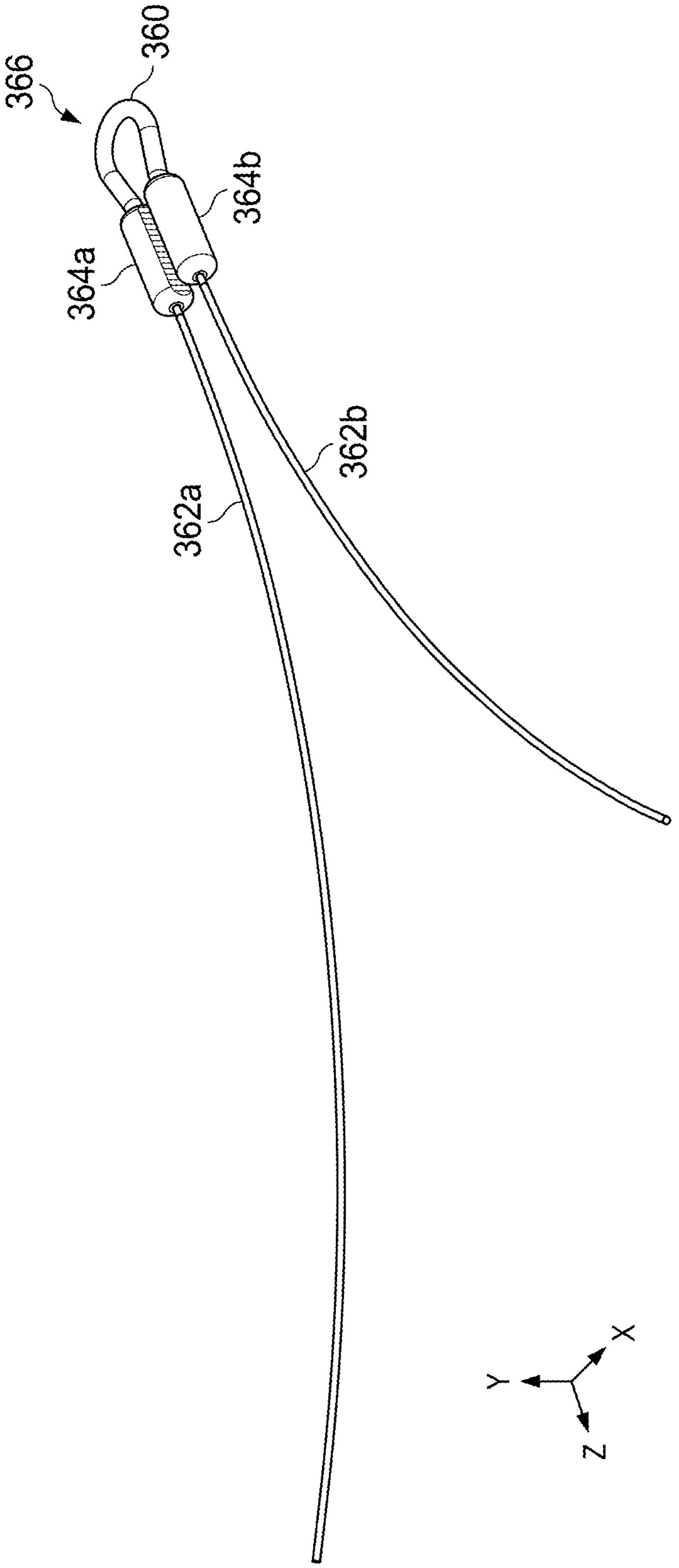
FIGS. 3D-3F are illustrations of an illustrative septal electrode to which extension electrodes extend and are supported by sleeves.
Figure 3E:
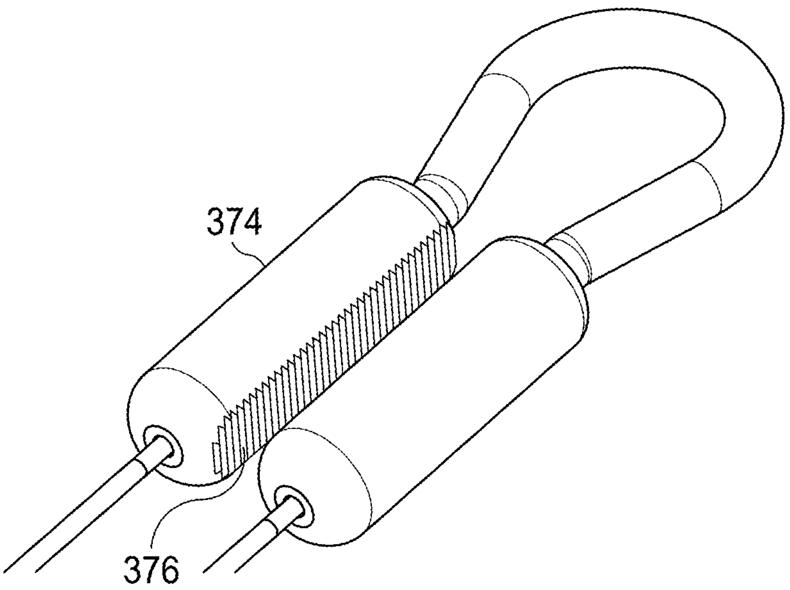
Figure 3F:
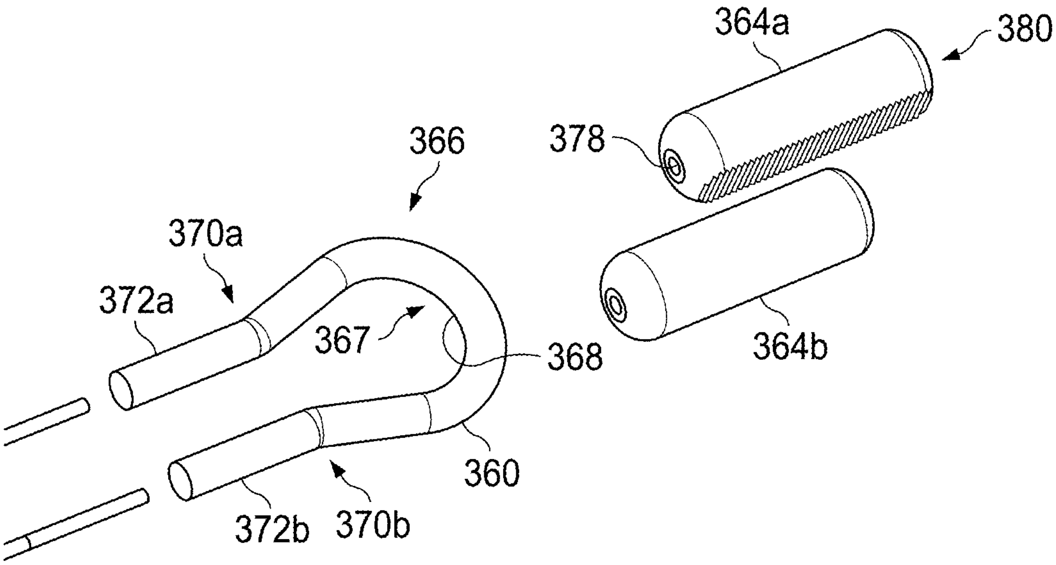

With regard to FIGS. 3D-3F, illustrations of an illustrative septal electrode 360 to which extension electrodes 362*a* and 362*b* (collectively 362) extend and are supported by sleeves 364*a* and 364*b* (collectively 364) are shown. In this embodiment, the septal electrode 360 is curved at an end region 366 to form a concave shape 367 along an inner radius surface 368 of the septal electrode 360 and opposing convex shapes 370*a* and 370*b* (collectively 370) at an intersection between the end region 366 and projection members 372*a* and 372*b* (collectively 372). The projection members 372 may extend parallel or substantially parallel (i.e., within a few degrees as limited by manufacturing processes) with one another. The overall shape of the septal electrode 360 may provide for more inward pressure being applied to a septum 250 by the sleeves 364 that extend over the projection members 372 than the end region 366. The sleeves 364 may be tubular and be identical in size and shape with one another. In an embodiment, the sleeves 364 may include a rounded external surface radially along the sleeves 364 and have flat surfaces 376 with a textured surface, such as a triangular, saw tooth, protrusions, indentations, hooked, and/or any other textured or geometric-shaped surface that causes the flat surfaces 376 to secure against the septum 250, thereby reducing slippage of the septal electrode 360 relative to the septum 250.

As shown, the sleeves 364 include openings 368 and 380, where the opening 378 may be sized to interference fit the extension electrodes 362 and the openings 380 may be configured to interference fit the projection members 372. The sleeves 374 may be non-conductive. The septal electrode 360 may be electrically conductive, and include a non-conductive coating or sleeve. Other configurations of the septal electrode 360 may be utilized. If conductive, electrical signals applied to one of the extension electrodes 362 (e.g., extension electrode 362*a*) by a pacemaker or other electrical power source (e.g., defibrillator) may flow through the septal electrode 360 to the other of the extension electrodes 362 (e.g., electrical conductors 362*b*), thereby applying electrical signals to the wall 252L of the left atria 235, where the extension electrode 362*b* may be in direct contact with one or more of the endocardium, myocardium, and/or epicardium of the wall 352L of the left atria 235.

Figure 4A:
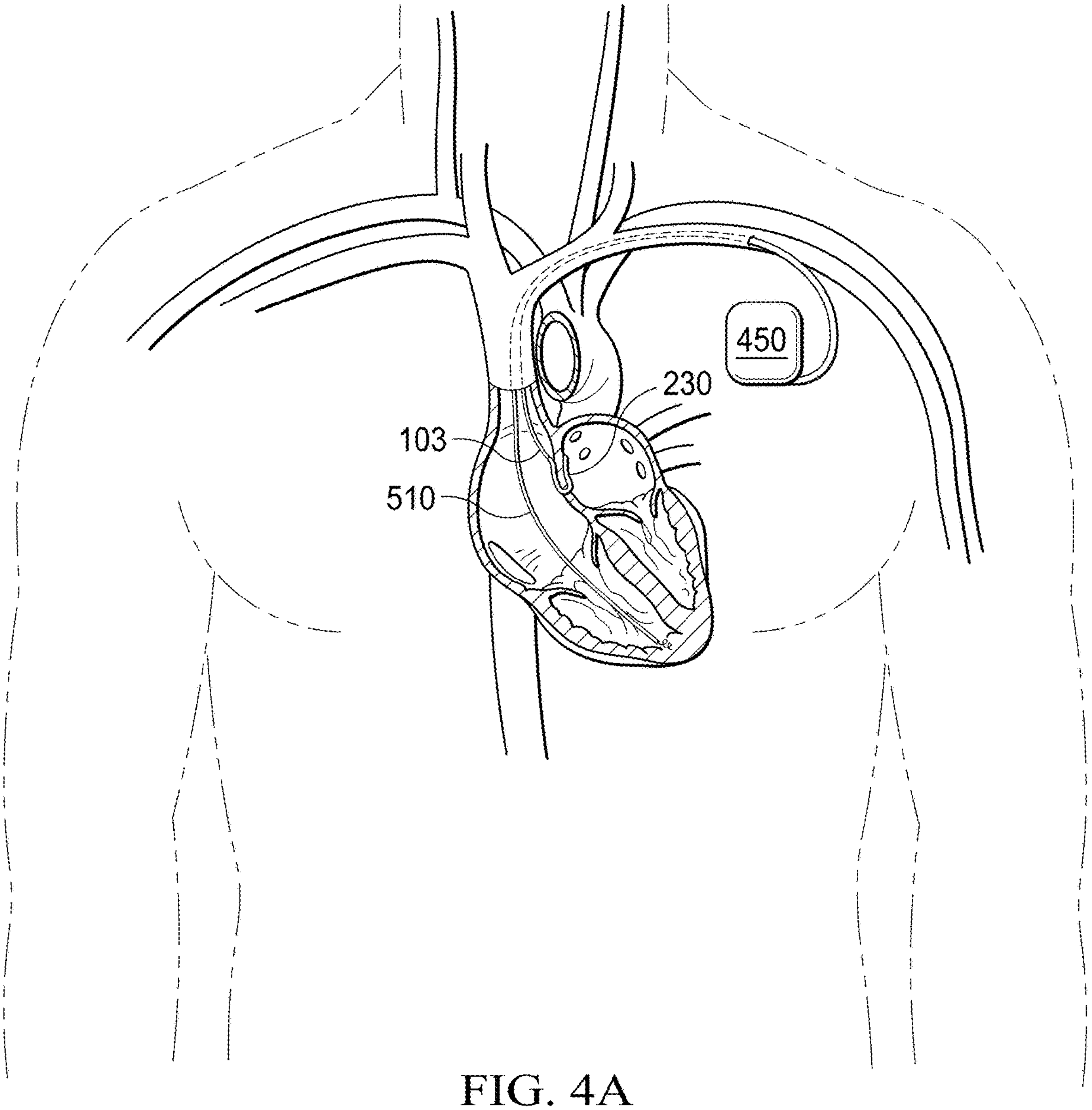
FIG. 4A shows an example of an implantable medical device with a septal electrode on one lead and another electrode on a second lead into the right ventricle.
Figure 4B:
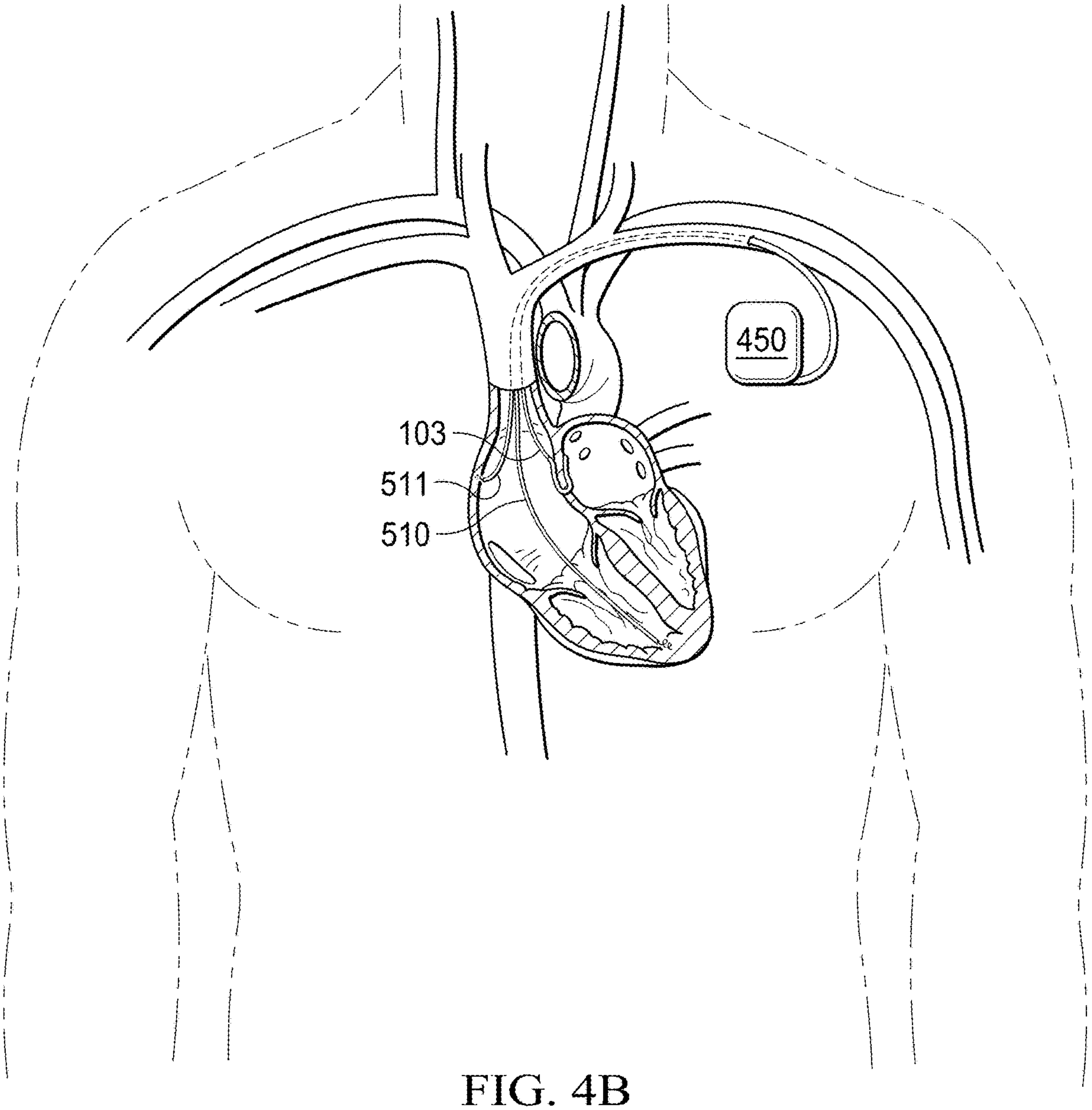
FIG. 4B shows an example of an implantable medical device with a septal electrode on one lead, and two additional leads anchored into the right atrium and right ventricle.

FIG. 4A shows an atrial defibrillator (or pacemaker, sensor, or recording device) implanted in a person with the septal electrode 230 of lead 103 connected to a battery-powered electronics enclosure 450 (similar to electronics enclosure 110 described above) and attached to the atrial septum and another lead 510 provided into and anchored to the right ventricle. The electronics enclosure comprises a sealed enclosure, a battery contained therein, and a circuit to generate electrical stimulation signals to be provided to the electrodes at the distal ends of the leads. FIG. 4B shows the atrial defibrillator implanted in a person with the septal electrode 230 of lead 103 attached to the atrial septum, a second lead 510 provided into and anchored to the right ventricle, and a third lead 511 anchored into the right atrium.

Figure 5:
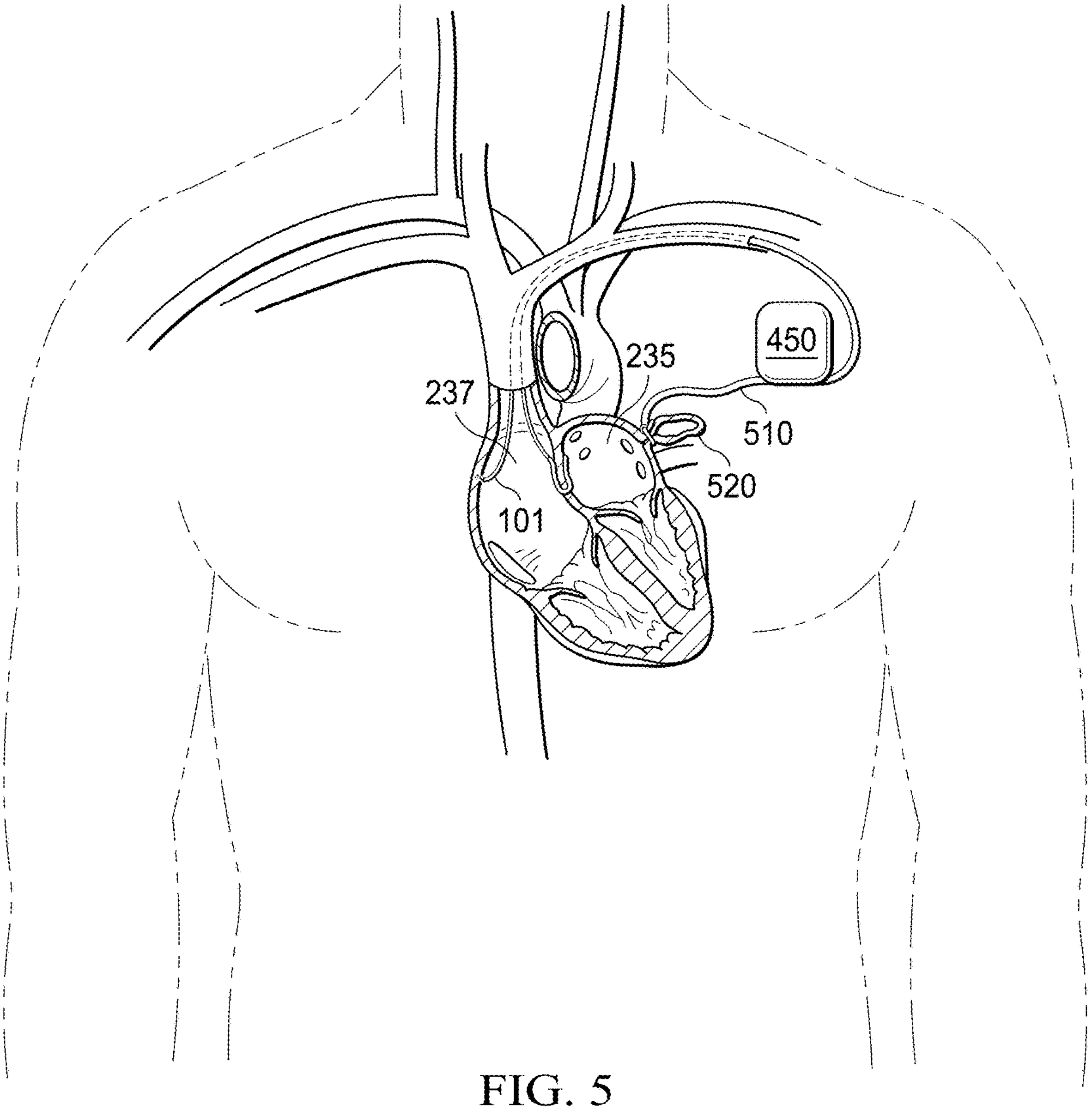
FIG. 5 illustrates another embodiment in which an electrode is part of an atrial appendage closure device in which the closure device is external to the atrial appendage, which keeps the wire of the device tight against the atrial wall.
Figure 6A:
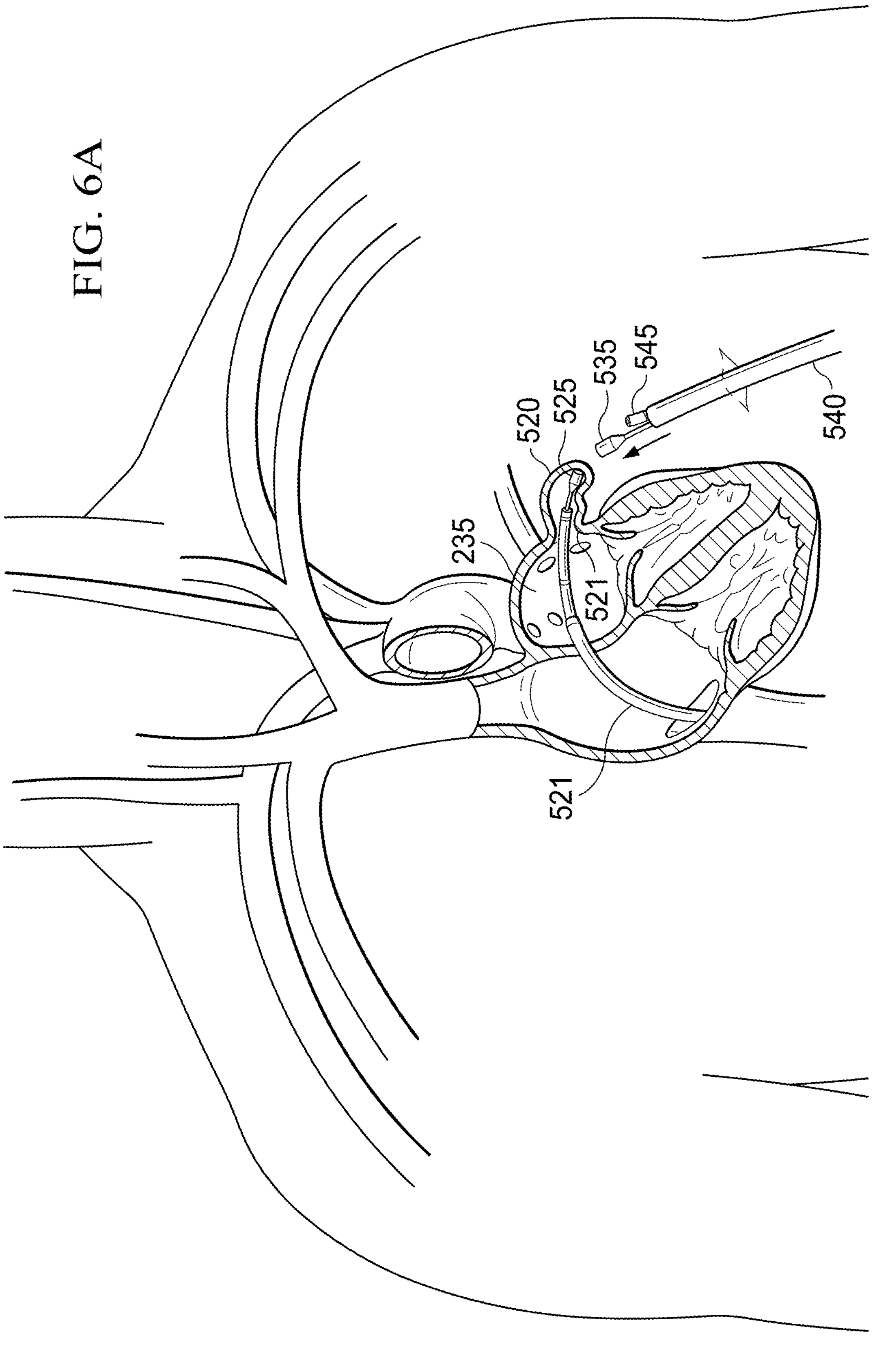
FIGS. 6A-6D illustrate a medical procedure for implanting the closure device and associated electrode of FIG. 5.
Figure 6B:
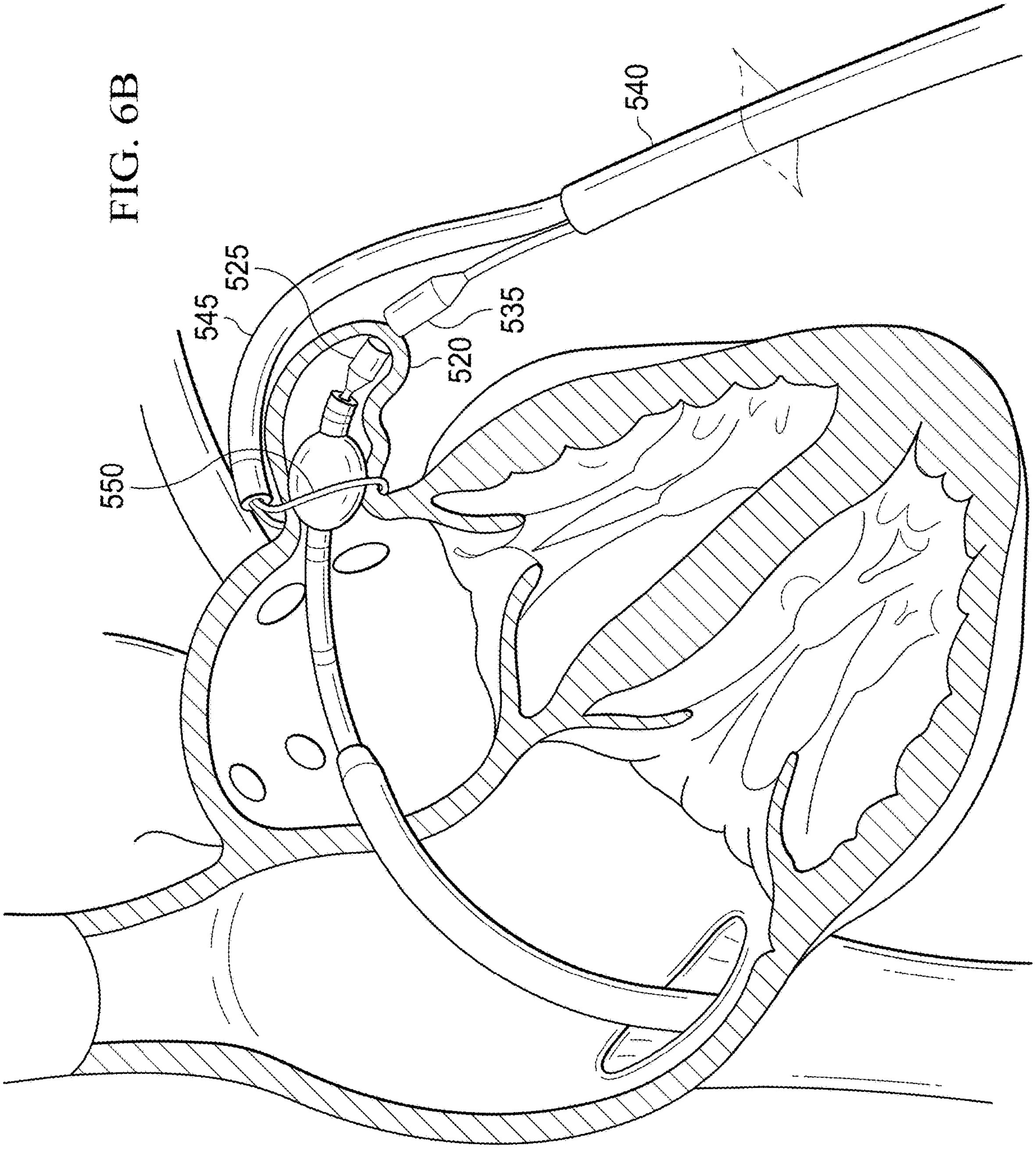
Figure 6C:
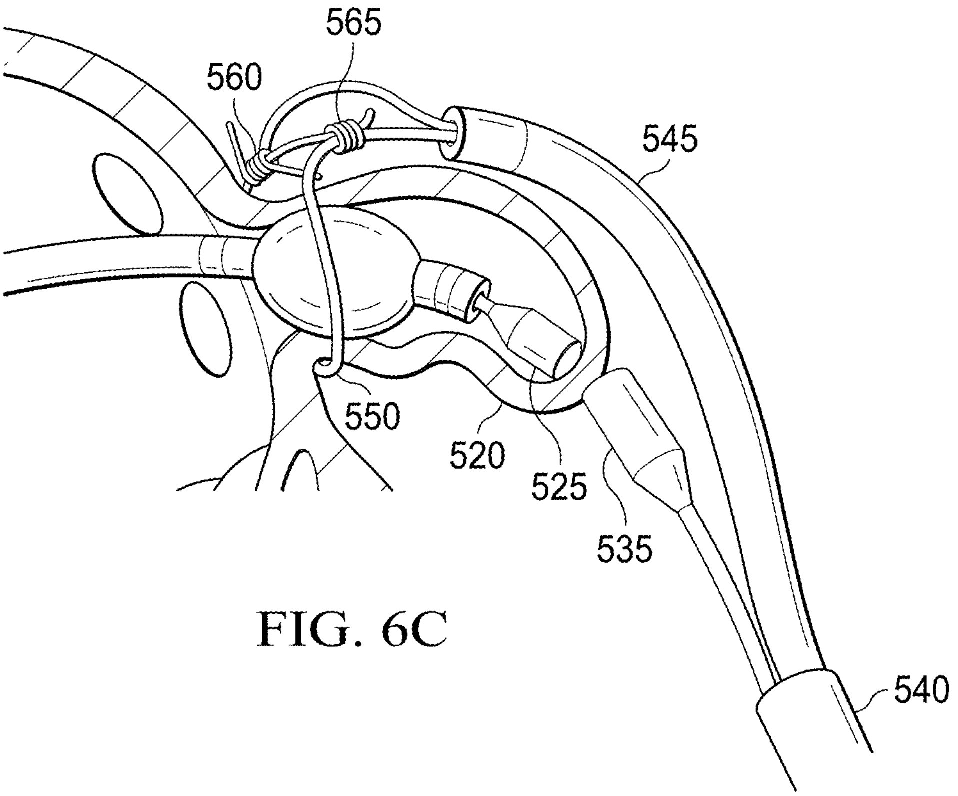
Figure 6D:
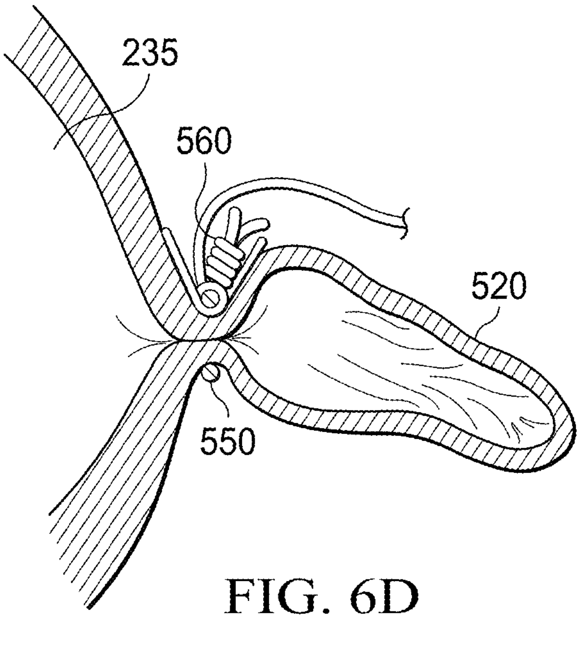
Figure 7:
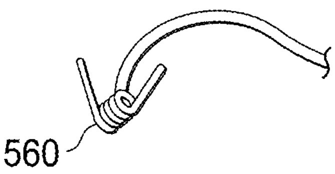
FIG. 7 shows a close-up view of one example of the electrode configured to be coupled to the atrial appendage closure device of FIG. 5.

FIGS. 5-7 illustrate an embodiment in which an atrial electrode is included in a device that occludes an orifice of the atrial appendage from outside the heart. FIG. 5 depicts an arrangement of the leads of a defibrillator with one atrial lead 101 placed in the right atrium 237. A second atrial lead 510 is placed in or about the atrial appendage 520 of the left atrium 235 and is attached to an atrial appendage closure device that is used to dose the orifice between the left atrium 235 and the atrial appendage 520. The leads 101 and 510 and their electrodes allow for specific atrial defibrillation of the atria, with a very small amount of energy (approximately 1-10 joules). The device extensions contain memory shaped metal or another composition, such as plastic, which holds the extensions tight against outside of the left atrium. FIG. 5 also shows the pulse generator 450 which comprises a sealed enclosure containing a battery and a circuit to generate the stimulation energy to electrodes at the distal end of the lead(s) 101 and 510.

FIG. 6A shows a portion of the procedure to implant an atrial appendage closure device around the atrial appendage 520. Installation of the atrial appendage closure device includes a magnet 525 positioned via a sheath 521 inside the atrial appendage 520. A second magnet 535 is brought near magnet 525 from outside the heart via a sheath 540 inserted through a small incision in the patient's chest. The orifice 521 is shown between the left atrium 235 and the atrial appendage 520. Once the magnet 535 is brought dose enough to magnet 525, the magnetic attraction causes the two magnets into contact with the wall of the atrial appendage 520 sandwiched therebetween. The magnets stabilize the atrial appendage 520. FIG. 6A also shows the distal end of a sheath 545 containing a lariat (discussed below).

FIG. 6B depicts the deployment of a lariat 550 around the base of the atrial appendage 520. The lariat 550 may be made of suture material or wire. FIG. 6C depicts a lead extension with electrodes 560 and 565 attached to the lariat 550. The electrodes can be placed on the lariat device before insertion into the body. The electrode array may vary depending on which configuration provides the optimal delivery of joules at the lowest resistance. There can be one or more electrodes fixed to the lariat. The electrodes may be longer and unfurl against the outside of the LA upon deployment. The covering or composition of the extensions contain memory shaped metal or other material that ensures the extensions remain in contact with the left atrium, or other epicardial surfaces. The specific length and number of electrodes and whether they unfurl depends on the energy needed to deliver the appropriate energy for defibrillation and the acceptable resistance generated. FIG. 6D shows the lariat 550 in place and cinched around the base of the of the atrial appendage 520 thereby closing off the orifice from the left atrium 525 into the atrial appendage. FIG. 6D also shows the electrode 560 positioned on the lariat 550 and thus just outside the left atrium.

FIG. 7 depicts the electrode 560 separate from the lariat 550. In this example, the electrode 550 is a coiled spring electrode. The electrode may unfurl and be present on the outside of the LAA base and or LA. There can be more than one electrode. The configuration can be a star or circle or other shape. However, the configuration of the electrode 560 may be other than that shown in FIG. 7 in other embodiments. In other examples, the portion of the electrode pressed against the left atrial tissue may be longer than that shown in FIG. 7 or there may be one or more additional electrodes on the lariat 550 to increase the surface area along the left atrium. The configuration of the electrode array may vary somewhat also to accommodate the size of the atrial appendage closure device.

FIGS. 8A-8D illustrate the closure of the orifice between the left atrium 235 and the atrial appendage 520 from inside the heart using a plug 810 (also referred to as a left atrial appendage occluder). The plug 810 is fitted with one or more electrodes connected to a pulse generator (e.g. pulse generator 450) and used for defibrillation. One or more other electrodes are positioned in the right atrium, right ventricle, left ventricle, coronary sinus, or intra-atrial septum. The plug 810 is deployed through a sheath 805.

Figure 8A:
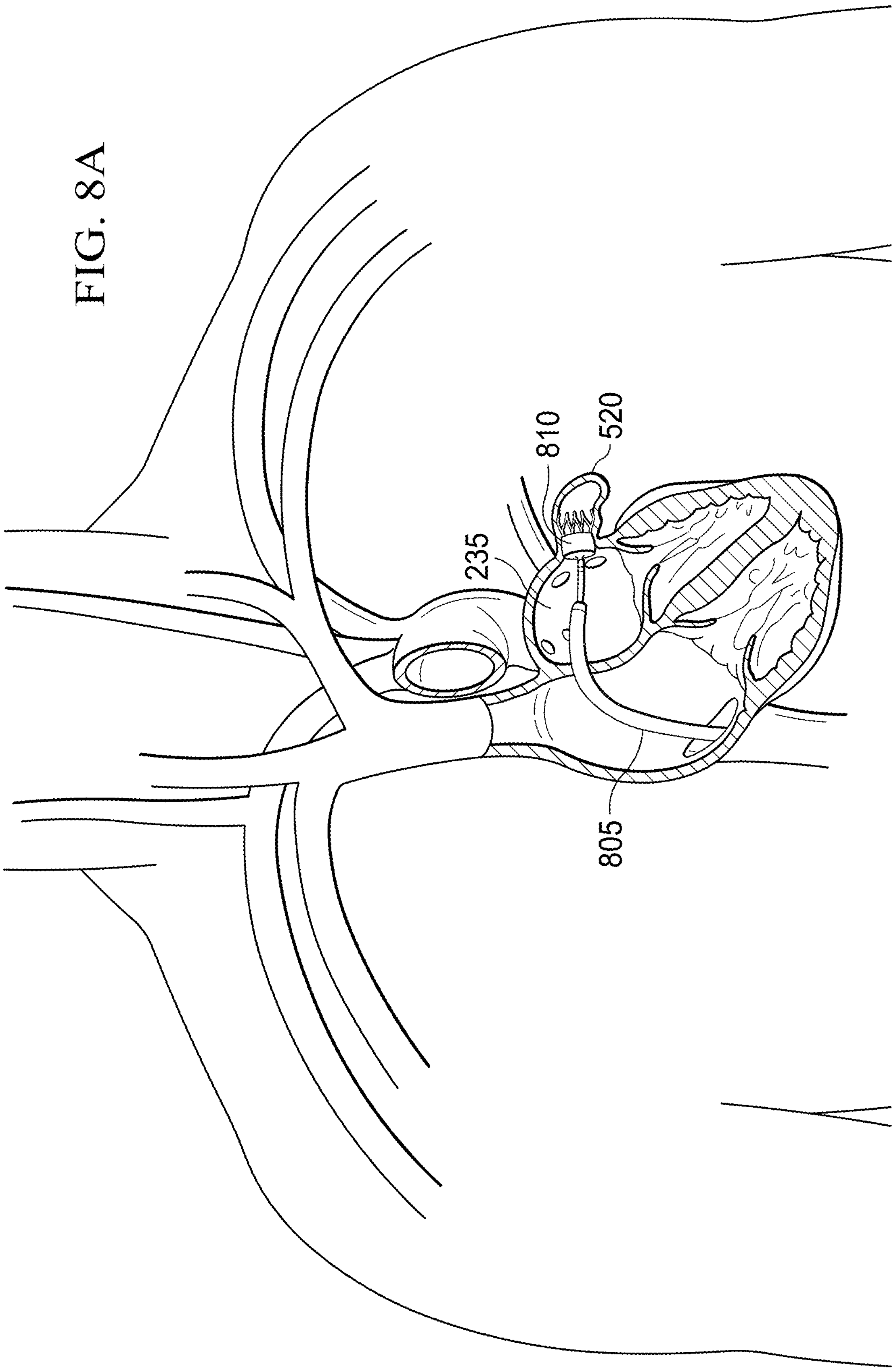
FIGS. 8A-8D illustrate another embodiment in which an electrode is part of an atrial appendage closure device in which the closure device is internal to the atrial appendage.
Figure 8B:
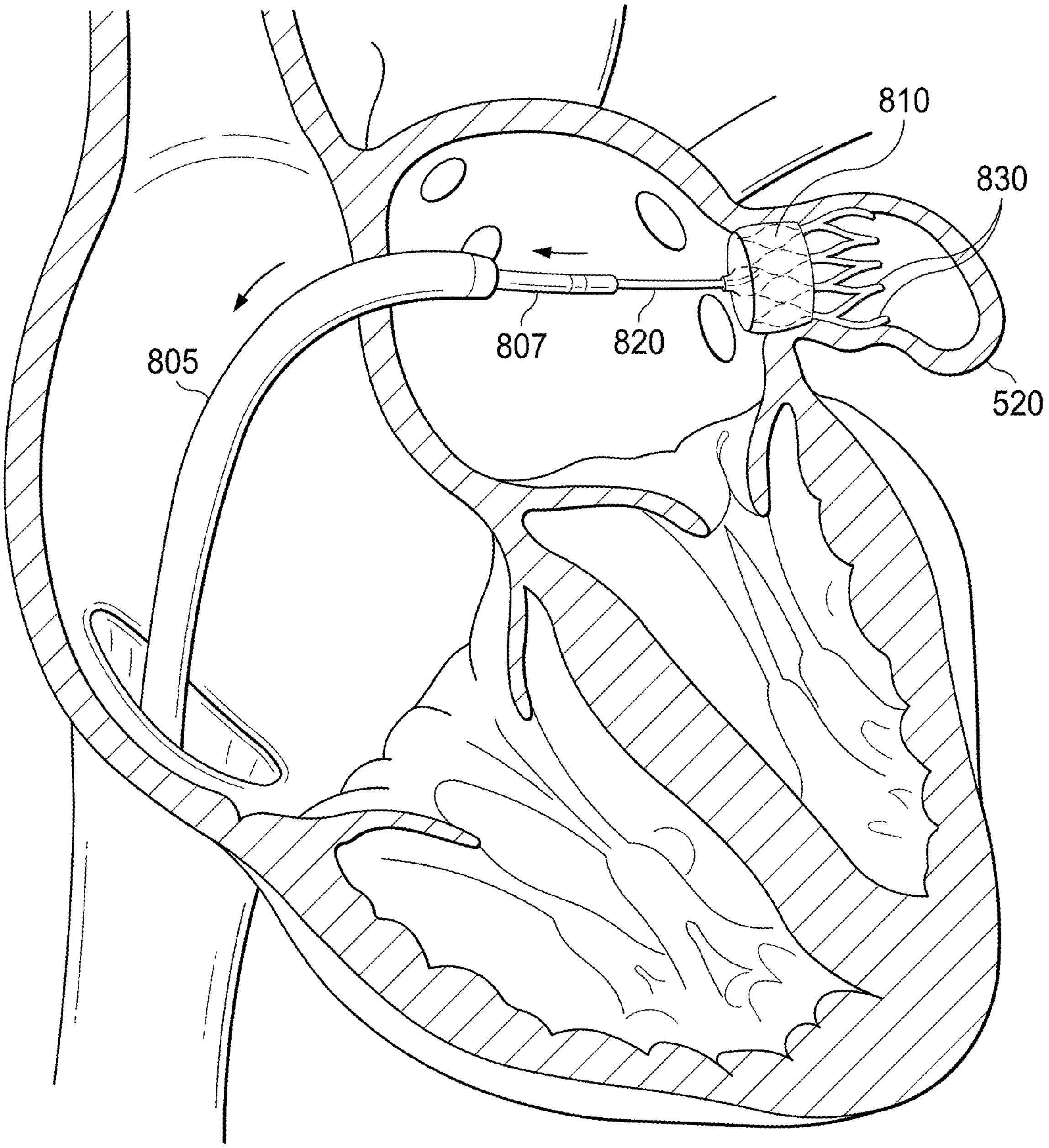

FIG. 8B shows the retraction of the sheath 805 and a plug deployment member 807. A lead 820 is shown inside the plug deployment member 807. The lead 820 is exposed when the sheath 805 and plug deployment member 807 are retracted. Electrodes 830 are shown on the lead 820 inside the atrial appendage 520. The device keeps the wires snugly against the inside heart walls, which keep the wires out of the flow of blood. In this position, the wires become embedded in the atrial wall.

Figure 8C:
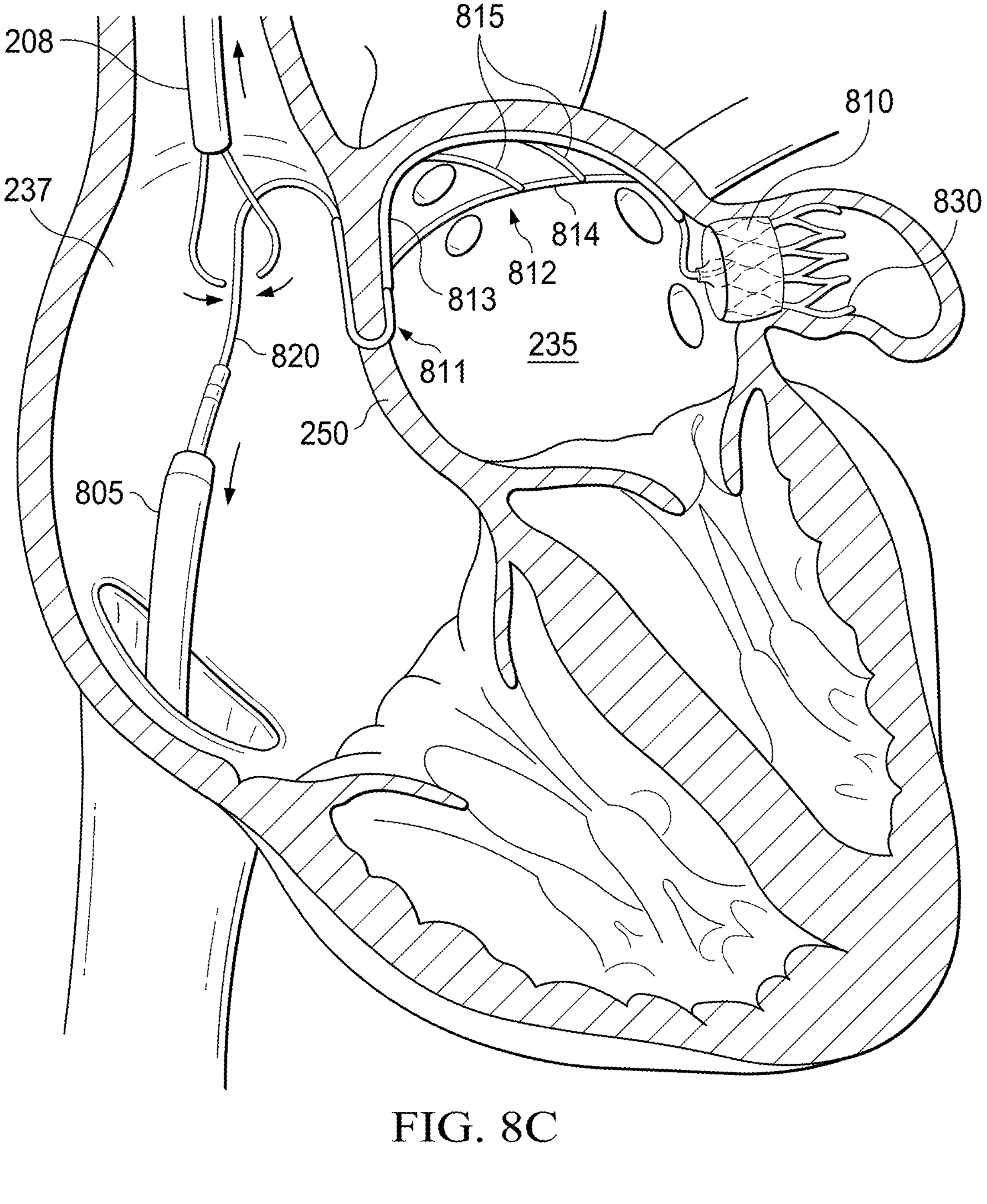

In FIG. 8C, the lead 820 from the left atrial closure device (plug 810) extends from the device and upon retraction of the sheath 805 and plug deployment member 807 brings the attached lead 820 into the right atrium 237. In the right atrium 237, the lead is then grasped or directed with a snare device 208 to be delivered into the left or right subclavian vein or other vein for connection to a pulse generator 450 that would be placed subcutaneously as described above. FIG. 8C also shows a lattice 812 coupled to a U-shaped dip 811 that is coupled to the septum 250. The lattice includes, for example, a first wire 812 and a second wire 813, both coupled to the U-shaped dip 811 and configured to be restrained against the endocardium of the left atrium 235. More than two wires can be included as desired. The wires 812 and 813 are interconnected and spaced apart by one or more interconnecting wires 815, also which are restrained against the wall of the left atrium. The U-shaped dip 811 and wires 813, 814, and 815 may be formed from any suitable type of shape memory metal, such as Nitinol.

Figure 8D:
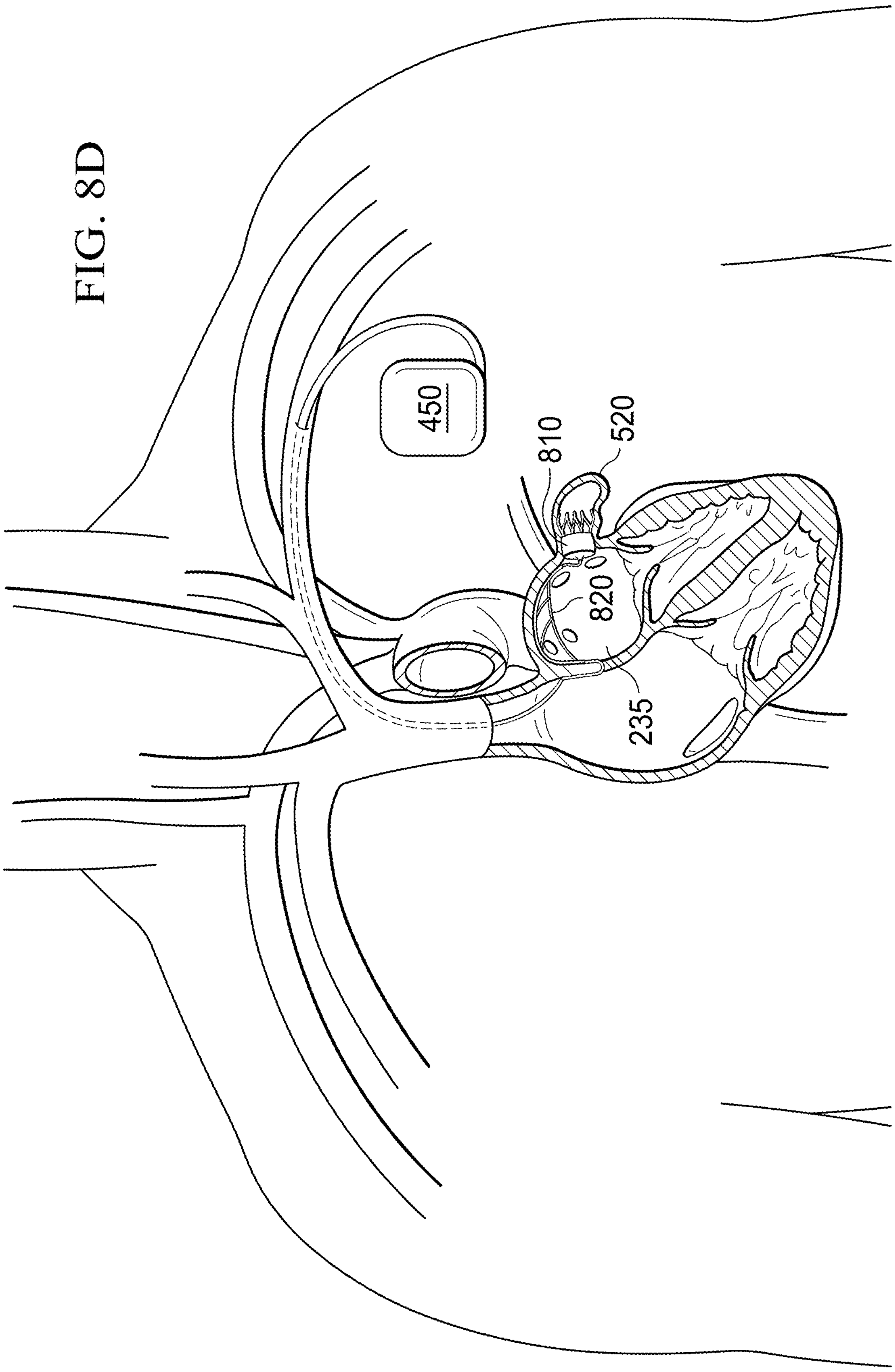

FIG. 8D shows the final configuration of plug 810 dosing off the atrial appendage 520 with the left atrial lead 820 extending from the left atrial closure device (plug 810), extending along and hugging the interior wall of the left atrium 235. The wire then traverses the atrial septum to the right atrium. The lead 820 then extends through the superior vena cava (alternatively, the inferior vena cava) to a more peripheral vein that would allow access to the pulse generator 450 (which may be configured to perform defibrillation and/or pacing). A right atrial (as in FIG. 1, lead 101) may also be present and connected to the pulse generator 450. Such additional lead could also be a lead positioned in, for example, the right ventricle, left ventricle, or coronary sinus lead.

In the example of FIGS. 8C and 8D, the active electrode (providing stimulation or sensing capability) can be provided on the lattice 812 (e.g., wire 814), in or on the plug 810, or on both the lattice and the plug. In one embodiment, the electrode is on one of wires 813 or 814 of the lattice 812, and the other wire 813, 814 of the lattice with its shape memory helps to force the electrode-carrying wire into continuous contact with the atrial wall. In one embodiment, the lattice 812 is present but not the plug 810. Further, the U-shaped dip 811 may or may not have an electrode. In one example, the dip 811 functions as an anchor for another structure (e.g., the lattice 812, a pacing lead, etc.) and is not itself used for sensing or stimulation purposes.

Figure 8E:
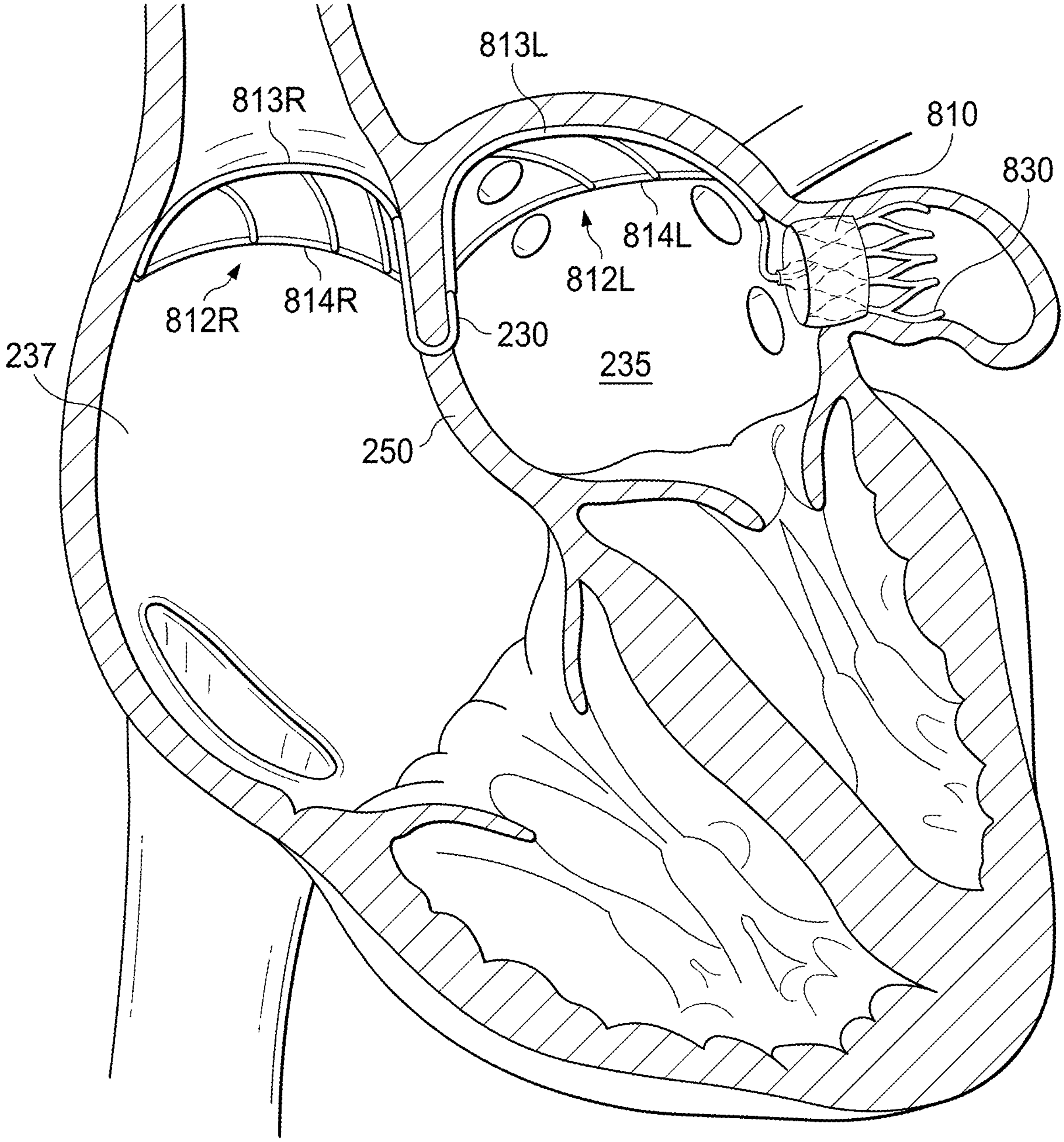
FIG. 8E is an illustration of an illustrative embodiment of another embodiment of extended electrodes that are integrated with respective lattices that are connected (electrically and physically) connected to the septal electrode.

With regard to FIG. 8E, an illustration of an illustrative embodiment of another embodiment of extended electrodes 813L and 813R (collectively 813) that are integrated with respective lattices 812L and 812R that are connected (electrically and physically) to the septal electrode 230 is shown. Wires 814L and 814R may also be configured with a shape preform (i.e., with a shape memory) to extend along and maintain contact with the endocardium of the respective left 235 and right 237 atria. In an embodiment, the wires may be non-insulated or partially insulated (e.g., insulation along a portion, along a side with the metal exposed on the other side for endocardium contact, or along a portion and along a side). Although not shown, the septal electrode 230 may be connected to a lead (e.g., lead 103 of FIG. 2J, for example) or to a leadless pacemaker (e.g., leadless pacemaker 260 of FIG. 2N) for providing electrical signals to the septal electrode 230 for delivering the electrical signals to the extended electrodes 813.

Figure 8F:
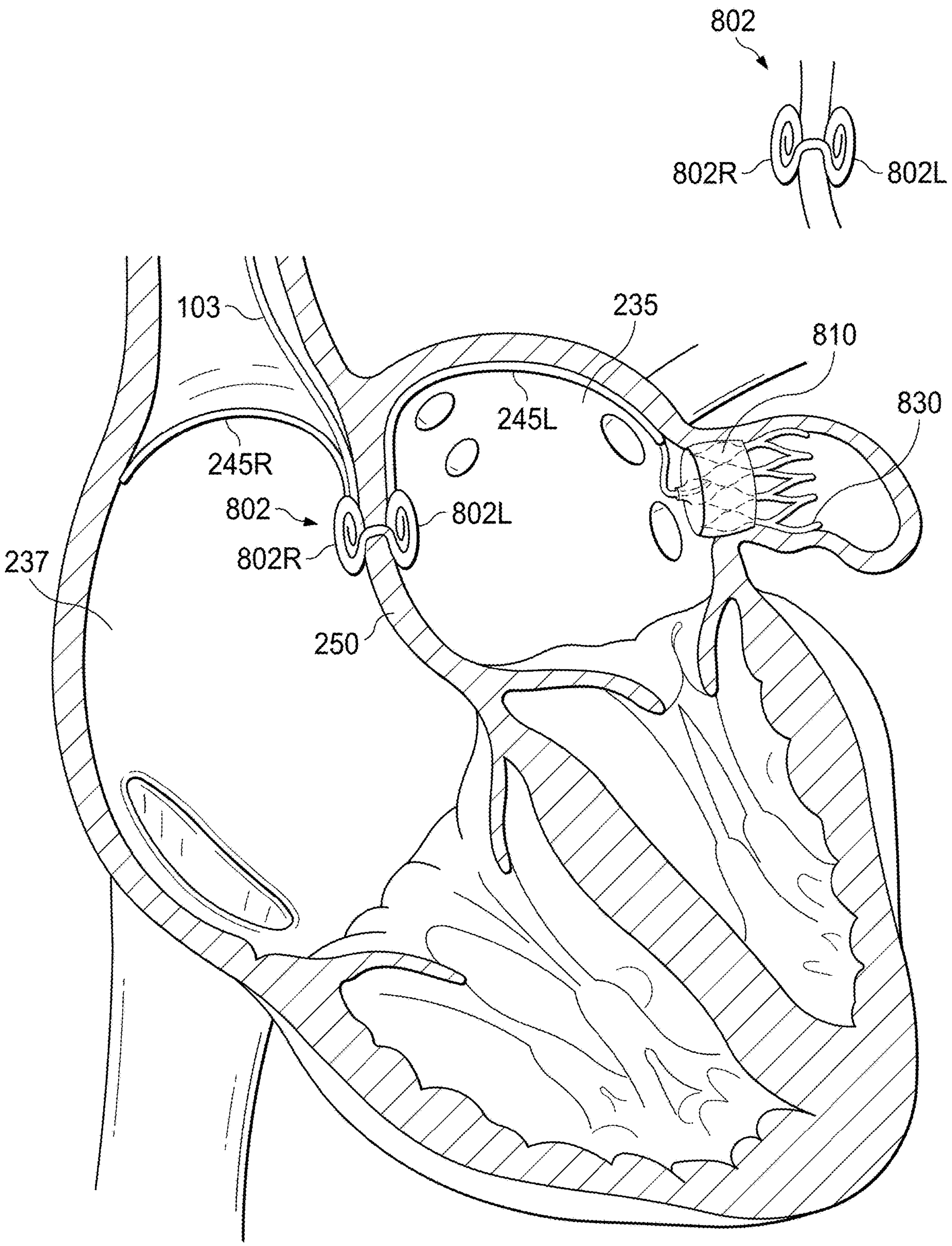
FIG. 8F is an illustration of alternative embodiment of a septal electrode configured as a pair of springs that form the septal electrode.

With regard to FIG. 8F, an illustration of an alternative embodiment of a septal electrode 802 configured as a pair of springs 802R and 802L that form the septal electrode 802 is shown. The springs 802R and 802L may function to hold the extension electrodes 245 along the atrial septum 250 and endocardium of the left and right atria 235 and 237. In this embodiment, a lead 103 may be electrically connected to the septal electrode 802. The springs 802R and 802L may be conductive or non-conductive. If non-conductive, a conductor may be integrated with the septal electrode 802 to provide for electrical connections with the lead 103 and extension electrodes 245. In an embodiment, opposing plates (not shown) may be disposed between the springs 802R and 802L that are used to hold the septal electrode 802 with the atrial septum 250. Protrusions (not show) may be positioned on the springs 802R and 802L (and/or plates) facing the atrial septum 250 to provide added support for maintaining the septal electrode 802 against the atrial septum 250. Although springs 802R and 802L are shown, it should be understood that only a single spring, such as spring 802L, may be utilized and the spring 802R may be a plate or other structural element. It should further be understood that a variety of configurations of the septal electrode 802 may be utilized to perform the same or similar functions in providing both electrical conductivity and support for the extension electrodes 245, as provided herein.

Figure 9:
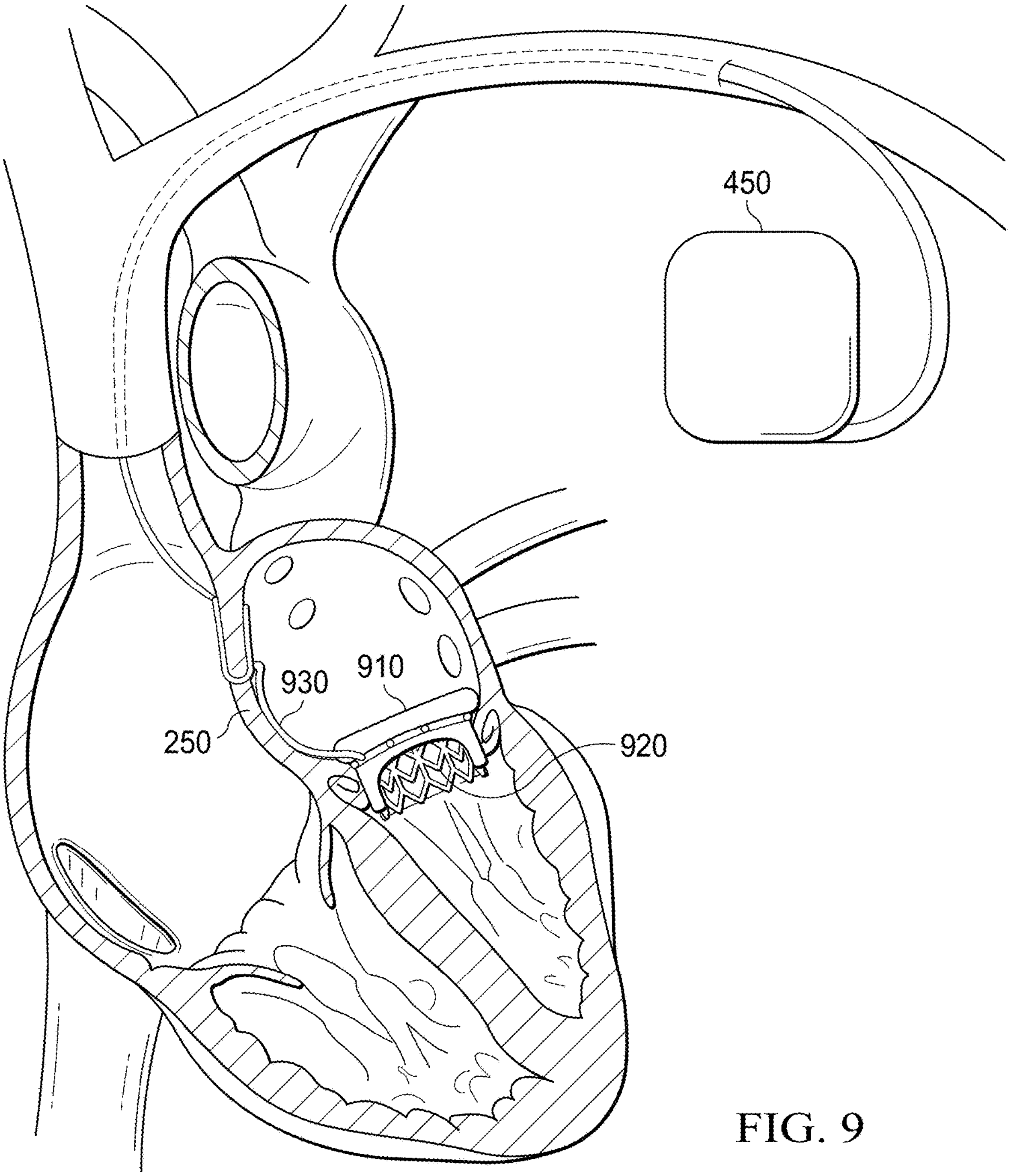
FIG. 9 shows an embodiment in which an electrode is part of a mitral valve device in which the wires are connected to the electrodes on the mitral annulus and hug the atrial septum, and connect to the electrode embedded in the septum.

In another embodiment, a left atrial lead can be incorporated a mitral valve replacement and/or mitral valve repair, either transseptal via a percutaneous approach or minimally invasive or open surgical approach. For example, an electrode array can be incorporated into mitral valve devices that touch or are near the left atrium. FIG. 9 shows a prosthetic mitral valve device 910 which is incorporated with one or more electrodes 920 forming an electrode array. The electrodes 920 are on the distal end of an atrial lead. The lead 930 would then be routed through the atrial septum 250 and connected to a pulse generator 450 as described above. The orifice of the mitral valve, where most mitral valve devices (such as mitral valve device 910) are positioned, is a suitable site for bi-atrial defibrillation with the device described herein. One configuration of the electrode array would be a conductive thin wire woven or otherwise attached to the valve device 910 as it sits around the mitral orifice. The mitral valve device 910 or devices may accommodate the electrode array and lead 930. Lead 930 can extend and overlap with the septal restraining device. The septal restraining device then connects to an insulated wire which connects to a pacemaker and/or defibrillator or transducer. The mechanical properties of the device hold the wires and extensions against the atrial wall, where tissue ingrowth will occur, as it does with the implanted mitral valve. The lead 930 can also allow attachment to another grasping device (e.g., snare device 208) to bring the wire to the appropriate site near the defibrillator/pacemaker pocket.

Referring further to FIGS. 3D-3F, one embodiment of installing the implantable device for treating AFIB may include clamping the septal electrode 360 on the septum 250 with extension electrodes 362 extending along the wall(s) 352R and 352L (e.g., along the endocardium, myocardium, and/or epicardium of the wall(s) 352R and 352L) is shown. Once clamped, measurements of heart electrical signals via the may be performed, wherein the heart electrical signals may include the R-wave, P-wave, S-wave, and/or any other segments of a heart electrical signal. Because the septal electrode 360 is configured to clamp to the septum 250, if the heart electrical signals have poor or lower than anticipated measurements (e.g., low amplitudes), then the projection members 372 may be separated such that the flat surfaces 376 of the sleeves 364 may be separated from the septum 250 and rotated to cause the extension electrodes 362 to be re-aligned and engage with different regions of the endocardium, for example. If the extension electrode 362*b* extends into the wall junction 352*j*, then the extension electrode 362*b* may be withdrawn and re-inserted into a different area to try and form a better contact location.

Figure 3G:
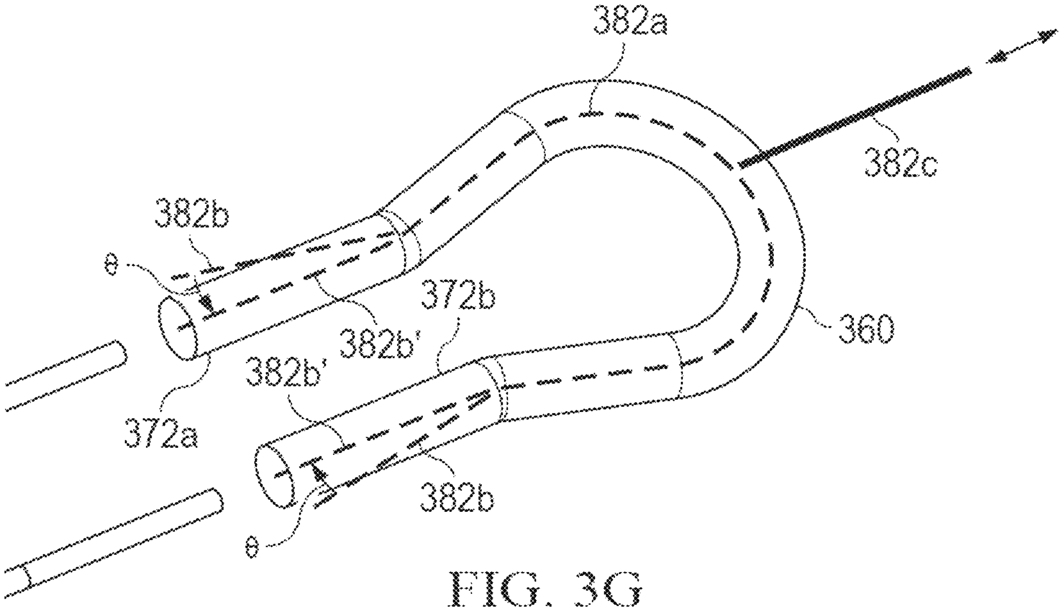
FIG. 3G is an illustration of an embodiment of the septal electrode that includes a center post with portions that extend therethrough.

With regard to FIG. 3G, an illustration of an embodiment of the septal electrode 360 that includes a center post 382 with portions 382*a*, 382*b*, 382*c* (collectively 382) that extends therethrough is shown. The center post 382 may be slid into and out of the septal electrode 360. The portions 382*b* may be biased outwards at an angle theta (0) such that when the portion 382*c* of the center post 382 is pulled out of the septal electrode 360, the projection members 372 rotate by the angle theta so as to be parallel with one another, thereby clamping to the septum 250. In the event that the extension electrodes 362 are not adequately conducting the heart electrical signals, then the operator may slide the center post 382 back into the septal electrode 360, thereby causing the portions 382*b* to spread the projection members 372 for rotating and re-clamping the septal electrode 360.

Some embodiments are directed to a support structure for a pacemaker lead. The support structure is coupled to the pacemaker lead and is configured to restrain a portion of the pacemaker lead against a person's atrial wall. Examples of the support structure are described herein and include, for example, a U-shaped dip, a lattice, etc. the support structure may comprise a shape memory material (e.g., Nitinol).

One embodiment of a process of manufacturing an implantable heart device may include forming a structure configured to be retained to an atrial septum. An extension electrode may be attached to a portion of the structure to cause the extension electrode to be positioned against the endocardium of the atrial septum, where the extension electrode may be configured to have an elongated portion thereof to maintain contact with the endocardium of the left atrium away from the atrial septum.

Attaching an extension electrode may include attaching an extension electrode formed of shape memory material. The process may further include connecting a lead to the structure to conduct electrical signals to the structure and extension electrode. Alternatively, a leadless pacemaker may be to the structure to apply electrical signals to the structure and extension electrode.

One embodiment of a process for implanting a heart device may include introducing an extension electrode into a blood vessel. The extension electrode may be traversed through the blood vessel and into the right atrium of a patient's heart. The extension electrode may be inserted through a right-side wall junction and into a wall of the left atrium so that the extension electrode is intramural with the left atrium.

The extension electrode may be secured to remain within the wall of the left atrium. Securing the extension electrode may include applying a structure to the atrial septum. Securing the extension electrode may include inserting a securing device into the right-side wall junction that prevents the extension electrode from exiting from the wall.

The process may further include extending a lead from the extension electrode, and connecting the lead to a pacemaker. Securing the extension electrode may include securing the extension electrode without causing the endocardium of the left atrium to be breached.

Using the structures described herein, a method for implanting a lead in the left side of a heart can comprise introducing the lead into a blood vessel, advancing the lead into a left atrium, fixing a distal region of the lead in position flush against the atrial septum with anchor elements on both sides of the atrial septum, and affixing an electrode on the lead in contact with the endocardium of the heart. Further, advancing the lead into the left atrium may include advancing the electrode beyond the septum and into continuous contact with the atrial wall. A lattice may be positioned in the left atrium to maintain the distal region of the lead in contact with the atrial wall.

Modifications are possible in the described embodiments, and other embodiments are possible, within the scope of the claims.

The invention claimed is:

1. An implantable medical device, comprising:

a cardiac lead having a distal region and a proximal end, the proximal end of the cardiac lead adapted to be coupled to an electronics enclosure, the distal region of the cardiac lead having a first electrode and a second electrode; and a structure configured to be implanted by being engaged with opposite sides of an atrial septum, the structure, when engaged with the opposite sides of the atrial septum, causing:

the first electrode of the distal region of the cardiac lead to (i) extend along the left side of the atrial septum and (ii) be in electrical communication with endocardium of the left atrium via the first electrode that extends away from the structure; and the second electrode of the distal region of the cardiac lead to (i) extend along the right side of the atrial septum and (ii) be in electrical communication with endocardium of the right atrium via the second electrode that extends away from the structure.

2. The implantable medical device of claim 1, wherein the structure comprises a septal closure device.

3. The implantable medical device of claim 1, wherein a first elongated portion of the first electrode extends along the left side of the atrial septum and further along the endocardium of the left atrium away from the atrial septum, and wherein a second elongated portion of the second electrode extends along the right side of the atrial septum and further along the endocardium of the right atrium away from the atrial septum.

4. The implantable medical device of claim 3, wherein the first electrode is supported by the structure and configured to extend away from and to maintain contact with the atrial septum and endocardium in the left atrium and the second electrode is supported by the structure and configured to extend away from and to maintain contact with the atrial septum and endocardium in the right atrium.

5. The implantable medical device of claim 4, wherein the distal region of the cardiac lead further includes a third electrode and a fourth electrode, the structure further causing the third electrode to extend along the left side of the atrial septum and the fourth electrode to extend along the right side of the atrial septum.

6. The implantable medical device of claim 1, wherein the structure comprises a shape memory material.

7. The implantable medical device of claim 1, wherein the structure includes protrusions configured to mate to the left and right sides of the atrial septum.

8. The implantable medical device of claim 1, wherein the structure includes a first portion, a second portion in parallel with the first portion, and a curved portion joining one end of the first and second parallel portions.

9. The implantable medical device of claim 8, wherein at least one of the first and second electrodes is on at least one of the first and second portions.

10. The implantable medical device of claim 1, wherein the distal region is coupled to the structure, and wherein the first and second electrodes are configured to have side surfaces restrained against the respective left and right sides of the atrial septum and endocardium in the left atrium and right atrium.

11. The implantable medical device of claim 10, wherein the first and second electrodes include protrusions extending along sides thereof are configured to mate to the endocardium.

12. The implantable medical device of claim 1, wherein the first and second electrodes are configured as part of respective lattices.

13. The implantable medical device of claim 12, wherein the lattice is configured to electrically couple the cardiac lead to the person's endocardium in both the left atrium and right atrium.

14. The implantable medical device of claim 12, wherein the first and second electrodes are on the respective lattices.

15. The implantable medical device of claim 12, wherein the structure is configured as a first portion, a second portion in parallel with the first portion, and a curved portion joining one end of the first and second portions, the first and second portions configured to attach to opposite sides of the atrial septum of the person and the curved portion is configured to extend through the atrial septum while the first and second portions are attached to the opposite sides of the atrial septum, and wherein the respective lattices include:

a first wire coupled to the first portion and configured to be restrained against the person's endocardium;

a second wire also coupled to the second portion and configured to be restrained against the person's endocardium; and an interconnecting wire connected to the first and second wires to space apart the first and second wires while restrained against the person's endocardium.

16. The implantable medical device of claim 1, wherein an elongated portion of the first electrode includes a plurality of electrodes that extend along the endocardium of the left atrium away from the atrial septum.

17. The implantable medical device of claim 16, wherein an elongated portion of the second electrode includes a second plurality of electrodes that extend along the endocardium of the right atrium away from the atrial septum.

18. The implantable medical device of claim 17, wherein the plurality of electrodes define a first lattice, and wherein the second electrodes define a second lattice.

19. The implantable medical device of claim 1, further including a mitral valve device, and at least one of the first and second electrodes are part of the mitral valve device.

20. The implantable medical device of claim 19, wherein:

the structure includes a first portion, a second portion in parallel with the first portion, and a curved portion joining the first and second portions, the first and second portions configured to be attached to opposite sides of the person's septum, the structure formed of a shape memory material; and the at least one of the first and second electrodes being coupled to a corresponding one of the first portion and second portion by way of a shape memory wire that is configured to be restrained against the person's endocardium between the mitral valve device and the structure.

* * * * *